US009895313B2

(12) United States Patent
Zhu et al.

(10) Patent No.: US 9,895,313 B2
(45) Date of Patent: Feb. 20, 2018

(54) COMBINATION LIPOSOMAL PHARMACEUTICAL FORMULATIONS

(71) Applicant: Cureport, Inc., Worcester, MA (US)

(72) Inventors: De-Min Zhu, Westborough, MA (US); Guoqiang Chen, Shrewsbury, MA (US)

( * ) Notice: Subject to any disclaimer, the term of this patent is extended or adjusted under 35 U.S.C. 154(b) by 0 days.

(21) Appl. No.: 15/059,972

(22) Filed: Mar. 3, 2016

(65) Prior Publication Data

US 2016/0256389 A1 Sep. 8, 2016

Related U.S. Application Data

(60) Provisional application No. 62/127,487, filed on Mar. 3, 2015.

(51) Int. Cl.
*A61K 47/28* (2006.01)
*A61K 9/127* (2006.01)
(Continued)

(52) U.S. Cl.
CPC .......... *A61K 9/1272* (2013.01); *A61K 9/0019* (2013.01); *A61K 9/1271* (2013.01); (Continued)

(58) Field of Classification Search
CPC .................................................... A61K 9/127
See application file for complete search history.

(56) References Cited

U.S. PATENT DOCUMENTS 4,898,735 A 2/1990 Barenholz et al.
5,013,556 A 5/1991 Woodle et al.
(Continued)

FOREIGN PATENT DOCUMENTS

EP 1 325 739 A1 7/2003
EP 1 214 078 B1 11/2004
(Continued)

OTHER PUBLICATIONS

Budman et al. (2002). "In vitro search for synergy and antagonism: evaluation of docetaxel combinations in breast cancer cell lines." Breast Cancer Research and Treatment, 74: 41-46.*
(Continued)

*Primary Examiner* — Benjamin Packard
(74) *Attorney, Agent, or Firm* — Nutter McClennen & Fish LLP; Konstantin Linnik

(57) ABSTRACT

Docetaxel and doxorubicin can be formulated in liposomal pharmaceutical compositions. In various embodiments, the pharmaceutical compositions include (i) a first liposome type comprising a first lipid layer comprising an unsaturated phospholipid, cholesterol or a cholesterol derivative, DC-cholesterol, a cationic lipid, and preferably a pegylated phospholipid, and a first active pharmaceutical ingredient (API) comprising docetaxel in the first lipid layer; and (ii) a second liposome type comprising a second lipid layer, an aqueous interior, and a second API comprising doxorubicin crystallized in the aqueous interior, (iii) where the first liposome type does not comprise doxorubicin and the second liposome type does not comprise docetaxel. The pharmaceutical composition can be used to treat a subject, for example, a human subject having cancer. The cancer can be, for example, a lung cancer, preferably non-small cell lung cancer (NSCLC), colon cancer, breast cancer, or liver cancer, preferably hepatocellular carcinoma (HCC).

20 Claims, 9 Drawing Sheets

Volume (%)
20
15
10
5
0
0.1 1 10 100 1000 10000
Size (d.nm)

(51) Int. Cl.

| | |
|---|---|
| ***A61K 31/337*** | (2006.01) |
| ***A61K 31/704*** | (2006.01) |
| ***A61K 9/00*** | (2006.01) |
| ***A61K 47/48*** | (2006.01) |
| *A61K 9/50* | (2006.01) |

(52) U.S. Cl.

CPC .......... *A61K 9/1277* (2013.01); *A61K 9/1278* (2013.01); *A61K 31/337* (2013.01); *A61K 31/704* (2013.01); *A61K 47/48815* (2013.01); *A61K 9/5084* (2013.01)

(56) References Cited

U.S. PATENT DOCUMENTS

| | | | |
|---|---|---|---|
| 5,264,618 | A | 11/1993 | Felgner et al. |
| 6,676,941 | B2 | 1/2004 | Thorpe et al. |
| 7,153,490 | B2 | 12/2006 | Parente Duena et al. |
| 7,511,016 | B2 | 3/2009 | Reutelingsperger |
| 7,850,990 | B2 | 12/2010 | Tardi et al. |
| 8,246,983 | B2 | 8/2012 | O'Halloran et al. |
| 8,293,240 | B2 | 10/2012 | Newell et al. |
| 8,404,681 | B2 | 3/2013 | Halbrook et al. |
| 8,476,242 | B2 | 7/2013 | Mon |
| 8,591,942 | B2 | 11/2013 | Javeri et al. |
| 8,747,869 | B2 | 6/2014 | Irvine et al. |
| 8,747,891 | B2 | 6/2014 | Kester et al. |
| 2004/0265367 | A1 | 12/2004 | Thorpe et al. |
| 2005/0202076 | A1* | 9/2005 | Mundus ............... A61K 9/1272 424/450 |
| 2006/0165744 | A1 | 7/2006 | Jamil et al. |
| 2006/0228694 | A1 | 10/2006 | Janoff et al. |
| 2007/0071804 | A1 | 3/2007 | Balu-Iyer et al. |
| 2008/0075762 | A1* | 3/2008 | Tardi .................... A61K 9/0019 424/450 |
| 2008/0107721 | A1 | 5/2008 | Lewis et al. |
| 2008/0286351 | A1 | 11/2008 | Ahmad et al. |
| 2008/0311182 | A1 | 12/2008 | Ferrari et al. |
| 2009/0053302 | A1 | 2/2009 | Boulikas |
| 2009/0098212 | A1 | 4/2009 | Fossheim et al. |
| 2009/0162425 | A1 | 6/2009 | Divi et al. |
| 2010/0034749 | A1 | 2/2010 | Schulze et al. |
| 2010/0099737 | A1 | 4/2010 | Krystal et al. |
| 2010/0104629 | A1 | 4/2010 | Dande et al. |
| 2010/0166872 | A1 | 7/2010 | Singh et al. |
| 2010/0297023 | A1 | 11/2010 | Miller et al. |
| 2010/0331819 | A1 | 12/2010 | Hossainy et al. |
| 2011/0070294 | A1 | 3/2011 | Javeri et al. |
| 2011/0177156 | A1 | 7/2011 | Szoka, Jr. et al. |
| 2011/0237686 | A1 | 9/2011 | Ng et al. |
| 2011/0250259 | A1 | 10/2011 | Buckman |
| 2011/0313017 | A1 | 12/2011 | Heyes |
| 2012/0082717 | A1 | 4/2012 | Char et al. |
| 2012/0128757 | A1 | 5/2012 | Kikuchi et al. |
| 2012/0141578 | A1 | 6/2012 | Robertson et al. |
| 2012/0225115 | A1 | 9/2012 | Au et al. |
| 2012/0294930 | A1 | 11/2012 | Ren et al. |
| 2012/0310142 | A1 | 12/2012 | Hossainy et al. |
| 2013/0102898 | A1 | 4/2013 | Kim et al. |
| 2013/0102993 | A1 | 4/2013 | Kim et al. |
| 2013/0115273 | A1 | 5/2013 | Yang et al. |
| 2013/0122056 | A1 | 5/2013 | Zhang et al. |
| 2013/0129812 | A1 | 5/2013 | Ozpolat et al. |
| 2013/0315986 | A1 | 11/2013 | Cheong et al. |
| 2013/0337066 | A1 | 12/2013 | Zhang et al. |
| 2013/0345286 | A1 | 12/2013 | Gollob et al. |
| 2014/0011759 | A1 | 1/2014 | Yaffe et al. |
| 2014/0024699 | A1 | 1/2014 | Kaelin, Jr. et al. |
| 2014/0187501 | A1 | 7/2014 | Bilodeau et al. |
| 2014/0271821 | A1 | 9/2014 | McGhee |
| 2014/0348900 | A1 | 11/2014 | Zhu |
| 2015/0299241 | A1 | 10/2015 | Chen et al. |
| 2016/0256387 | A1 | 9/2016 | Zhu et al. |

FOREIGN PATENT DOCUMENTS

| | | | |
|---|---|---|---|
| EP | 1 537 858 | A1 | 6/2005 |
| EP | 2 215 107 | B1 | 10/2012 |
| EP | 1 915 374 | B1 | 4/2014 |
| WO | 02/072068 | A2 | 9/2002 |
| WO | 02/085311 | A2 | 10/2002 |
| WO | 2005/053642 | A1 | 6/2005 |
| WO | 2006/055697 | A2 | 5/2006 |
| WO | 2007/072221 | A2 | 6/2007 |
| WO | 2008/021908 | A2 | 2/2008 |
| WO | 2008/039188 | A1 | 4/2008 |
| WO | 2009/051712 | A1 | 4/2009 |
| WO | 2010/009186 | A1 | 1/2010 |
| WO | 2010/065329 | A2 | 6/2010 |
| WO | 2010/108934 | A1 | 9/2010 |
| WO | 2011/115684 | A2 | 9/2011 |
| WO | 2011/120023 | A1 | 9/2011 |
| WO | 2011/134675 | A1 | 11/2011 |
| WO | 2012/015901 | A1 | 2/2012 |
| WO | 2012/021383 | A2 | 2/2012 |
| WO | 2012/170284 | A1 | 12/2012 |
| WO | 2013/012891 | A1 | 1/2013 |
| WO | 2013/052167 | A2 | 4/2013 |
| WO | 2013/066440 | A1 | 5/2013 |
| WO | 2013/155341 | A1 | 10/2013 |
| WO | 2013/188763 | A1 | 12/2013 |
| WO | 2014/015027 | A1 | 1/2014 |
| WO | 2014/057432 | A2 | 4/2014 |
| WO | 2014/071406 | A1 | 5/2014 |
| WO | 2014/079300 | A1 | 5/2014 |
| WO | 2014/093631 | A1 | 6/2014 |

OTHER PUBLICATIONS

Fritze et al. (2006). "Remote loading of doxorubicin into liposomes driven by a transmembrane phosphate gradient." Biochimica et Biophysica Acta, 1758: 1633-1640.*

International Search Report for Application No. PCT/US2016/020647, dated May 5, 2016. (12 pages).

International Search Report for Application No. PCT/US2016/020654, dated May 5, 2016. (11 pages).

Alexopoulos, A., et al., Phase II study of pegylated liposomal doxorubicin (Caelyx) and docetaxel as first-line treatment in metastatic breast cancer. Ann Oncol. Jun. 2004;15(6):891-5.

De La Flouchardiere, C., et al., Docetaxel and pegylated liposomal doxorubicin combination as first-line therapy for metastatic breast cancer patients: results of the phase II GINECO trial CAPYTTOLE. Ann Oncol. Dec. 2009;20(12):1959-63. doi: 10.1093/annonc/mdp231. Epub Jun. 25, 2009.

Livi, L., et al., Non-pegylated liposomal doxorubicin in combination with cyclophosphamide or docetaxel as first-line therapy in metastatic breast cancer: a retrospective analysis. Tumori. Jul.-Aug. 2009;95(4):422-6.

Sparano, J.A., et al., Phase I trial of pegylated liposomal doxorubicin and docetaxel in advanced breast cancer. J Clin Oncol. Jun. 15, 2001;19(12):3117-25.

Sparano, J.A., et al., Pegylated liposomal doxorubicin plus docetaxel significantly improves time to progression without additive cardiotoxicity compared with docetaxel monotherapy in patients with advanced breast cancer previously treated with neoadjuvant-adjuvant anthracycline therapy: results from a randomized phase III study. J Clin Oncol. Sep. 20, 2009;27(27):4522-9. doi: 10.1200/JCO.2008.20.5013. Epub Aug. 17, 2009.

Wolff, A.C., et al., Phase II trial of pegylated liposomal doxorubicin plus docetaxel with and without trastuzumab in metastatic breast cancer: Eastern Cooperative Oncology Group trial E3198. Breast Cancer Res Treat. May 2010;121(1):111-20. doi: 10.1007/s10549-010-0838-7. Epub Mar. 24, 2010.

Cresta, S. et al., "A randomized phase II study of combination, alternating and sequential regimens of doxorubicin and docetaxel as first-line chemotherapy for women with metastatic breast cancer," Annals of Oncol., 2004, v. 15, pp. 433-439.

(56) References Cited

OTHER PUBLICATIONS

Miller, K. D. et al., "Combination Versus Sequential Doxorubicin and Docetaxel as Primary Chemotherapy for Breast Cancer: A Randomized Pilot Trial of the Hoosier Oncology Group," J. Clin. Oncol., 1999, v. 17, pp. 3033-3037.

Nabholtz, J-M, et al., "Docetaxel and Doxorubicin Compared With Doxorubicin and Cyclophosphamide as First-Line Chemotherapy for Metastatic Breast Cancer: Results of a Randomized, Multicenter, Phase III Trial," J. Clin. Oncol., 2003, v. 21, pp. 968-975.

von Minckwitz, G., et al., "Doxorubicin With Cyclophosphamide Followed by Docetaxel Every 21 Days Compared With Doxorubicin and Docetaxel Every 14 Days as Preoperative Treatment in Operable Breast Cancer: The GEPARDUO Study of the German Breast Group," J. Clin. Oncol., 2005, v. 23, pp. 2676-2685.

Immordino, M.L., et al., Preparation, characterization, cytotoxicity and pharmacokinetics of liposomes containing docetaxel. J Control Release. Sep. 4, 2003;91(3):417-29.

Zhao, L., et al., Solid dispersion and effervescent techniques used to prepare docetaxel liposomes for lung-targeted delivery system: in vitro and in vivo evaluation. J Drug Target. Apr. 2011;19(3):171-8. doi: 10.3109/10611861003801859. Epub Apr. 30, 2010.

[No Author Listed] Prescribing Information, DOXIL, revised May 2007, Manuf. Ben Venue Laboratories, pp. 1-33.

[No Author Listed] Prescribing Information TAXOTERE, revised May 2010, Sanofi-Aventis U.S. LLC, pp. 1-62.

Deeken, J. F., et al., A phase I study of liposomal-encapsulated docetaxel (LE-DT) in patients with advanced solid tumor malignancies.

Haran, G. et al., "Transmembrane ammonium sulfate gradients in liposomes produce efficient and stable entrapment of amphipathic weak bases," Biochim et Biophys Acta, 1993, v. 1151, pp. 201-215.

Lewrick, F. et al., "Remote Loading of Anthracyclines into Liposomes," in Methods in Molecular Biology, V. Weissig, ed.; 2010, v. 605, Chapter 9, pp. 139-145.

[No Author Listed] Final Office Action dated May 30, 2017, for U.S. Appl. No. 15/059,943.

* cited by examiner

COMBINATION LIPOSOMAL PHARMACEUTICAL FORMULATIONS

CROSS-REFERENCE TO RELATED APPLICATIONS

This application claims the benefit of U.S. Provisional Application No. 62/127,487, filed Mar. 3, 2015, which is hereby incorporated by reference in its entirety.

FIELD OF THE INVENTION

The present invention generally relates to liposomal pharmaceutical compositions and, in various embodiments, more specifically to liposomal pharmaceutical compositions including two different active pharmaceutical ingredients (API) in two different liposome types (e.g., a first liposome type comprising a first API such as docetaxel, and a second liposome type comprising a second API such as doxorubicin).

BACKGROUND

Liposome technology has been utilized for drug delivery in clinical therapy and scientific research. To date, a handful of liposomal pharmaceutical formulations have been approved by the US Food and Drug Administration ("FDA"), and a number of new liposomal formulations are in clinical trials. However, the field of liposomal formulation is still evolving and each active pharmaceutical ingredient ("API") presents unique challenges.

One area where liposomal formulations can be applied is in cancer APIs. For example, liposomal formulations of doxorubicin are presently available under the trade names Doxil® and Myocet®. Doxil® is a pegylated (polyethylene glycol coated) liposome-encapsulated form of doxorubicin formerly made by Ben Venue Laboratories in the United States for Janssen Products, LP, a subsidiary of Johnson & Johnson. Myocet® is a non-pegylated liposomal doxorubicin made by Enzon Pharmaceuticals for Cephalon in Europe and for Sopherion Therapeutics in the United States and Canada. Myocet® is approved in Europe and Canada for treatment of metastatic breast cancer in combination with cyclophosphamide, but is not yet approved by the FDA for use in the United States.

Despite the handful of approved liposomal pharmaceutical formulations, the field is still limited by the currently available methods of making liposomal formulations, which present difficult problems associated with scalability and production costs. There exists a need for improved liposomal formulations for use in drug delivery.

SUMMARY OF THE INVENTION

In various aspects and embodiments, the invention provides a pharmaceutical composition including a first liposome type comprising a first API (e.g., docetaxel) and a second liposome type comprising a second API (e.g., doxorubicin). In various embodiments, (i) the first liposome type comprises a first lipid layer comprising an unsaturated phospholipid, cholesterol, and preferably a pegylated phospholipid, and a first active pharmaceutical ingredient (API) (e.g., docetaxel) in the first lipid layer; and (ii) a second liposome type comprising a second lipid layer, an aqueous interior, and a second API (e.g., crystallized doxorubicin) in the aqueous interior. The first liposome type does not comprise the second API (e.g., doxorubicin) and the second liposome type does not comprise the first API (e.g., docetaxel). The liposomes can be used to treat a subject, for example, a human subject having cancer. The cancer can be, for example, a lung cancer, preferably non-small cell lung cancer (NSCLC); colon cancer; breast cancer; or liver cancer, preferably hepatocellular carcinoma (HCC).

The invention can provide for increased efficacy and/or decreased toxicity, for example relative to (i) other pharmaceutical compositions where the first drug (e.g., docetaxel) and/or the second drug (e.g., doxorubicin) are not in a liposomal formulation. The invention can also provided superior results to known liposomal, and non-liposomal, formulation (e.g., Doxil® and Myocet®, or Taxotere®).

The invention can provide for targeted delivery of both the first and second API, for example to the liver. The invention can mitigate undesired side effects, for example by providing for increased drug loading, thereby reducing the amount of liposomes needed to deliver a quantity of the first drug (e.g., docetaxel) and the second drug (e.g., doxorubicin). Also, because the second drug (e.g., doxorubicin) is crystallized in the second liposome type, the second drug can have more targeted delivery and less off-target side effects.

Furthermore, because the first and second API are in separate liposomes, each liposome can be designed specifically for the API it carries. The different combinations of the two liposomal formulations, including different API ratio, different dosing sequence and interval time, can be clinically identified for the treatment of different type of cancers. It also provides physicians a flexibility to adjust the ratios of the two liposomal APIs at patients' bedside to optimize the outcomes while minimizing the adverse reactions for individual patients.

The invention provides a pharmaceutical composition comprising: (i) a first liposome type comprising a first lipid layer comprising an unsaturated phospholipid, cholesterol, and preferably a pegylated phospholipid, and a first active pharmaceutical ingredient (API) comprising docetaxel in the first lipid layer; and (ii) a second liposome type comprising a second lipid layer, an aqueous interior, and a second API comprising doxorubicin crystallized in the aqueous interior. The first liposome type does not comprise doxorubicin and the second liposome type does not comprise docetaxel.

In various embodiments, the first lipid layer and/or the second lipid layer consist of unsaturated phospholipid and cholesterol.

In various embodiments, the first lipid layer and/or the second lipid layer consist of unsaturated phospholipid, cholesterol, cationic lipid, and pegylated phospholipid.

In various embodiments, the first lipid layer and the second lipid layer comprise different lipid compositions (e.g., different lipid components and/or different amounts of certain lipid components). In various embodiments, the first liposome and the second liposome are different (e.g., in addition to comprising different APIs, derived from different lipid solutions and/or aqueous solutions as described below). Alternatively, in some embodiments, the first and second lipid layers are essentially the same (e.g., other than comprising different APIs, comprising essentially the same lipid components and amounts thereof).

In various embodiments, docetaxel is the only API in the first liposome type and/or doxorubicin is the only API in the second liposome type.

In various embodiments, the first lipid layer and/or the second lipid layer comprise: about 20-75%, preferably about 30-60%, (molar) unsaturated phospholipid; about 10-60%, preferably 20-50%, (molar) cholesterol; about 5-75%, preferably about 10-60%, (molar) cationic lipid; and about 0-20%, preferably 1-10%, (molar) pegylated phospholipid.

In various embodiments, the molar ratio of the first lipid layer components:doxorubicin is about 100:1 to about 2:1, preferably about 20:1 to about 5:1; and the molar ratio of the second lipid layer components:docetaxel is about 100:1 to about 2:1, preferably about 20:1 to about 5:1.

In various embodiments, the molar ratio of doxorubicin: docetaxel is about 10:1 to 1:10, preferably about 5:1 to 1:5, and more preferably about 3:1 to 1:3.

In various embodiments, the unsaturated phospholipid comprises a polyunsaturated phospholipid or a monounsaturated phospholipid, preferably a phosphatidylcholine, and more preferably and soy phosphatidylcholine or 1,2-dioleoyl-sn-glycero-3-phosphatidylcholine (DOPC).

In various embodiments, the cholesterol comprises a cholesterol derivative, preferably a cationic cholesterol derivative, more preferably an amino cholesterol derivative, and still more preferably dimethylaminoethanecarbamoyl-cholesterol (DC-cholesterol).

In various embodiments, the pegylated phospholipid comprises a phosphoethanolamine, preferably a 1,2-distearoyl-sn-glycero-3-phosphoethanolamine (DSPE) and wherein the pegylation is a PEG 500 to PEG 3000, preferably PEG 2000.

In various embodiments, the pharmaceutical composition is formulated for intravenous administration.

In various embodiments, the Z-average particle size of the liposomes is about 10-200 nm, preferably about 15-150 nm, and more preferably about 20-120 nm.

In various embodiments, upon intravenous administration to a subject, at least about 10% of the composition is delivered to the liver.

In various embodiments, the pharmaceutical composition is for use as a medicament.

In various embodiments, the pharmaceutical composition is for use as a cancer therapeutic.

The invention also provides a pharmaceutical composition consisting of: (i) a plurality of liposomes of the first type as described or claimed herein; (ii) a plurality of liposomes of the second type as described or claimed herein; and (iii) one or more pharmaceutical excipients.

The invention also provides a method of making the pharmaceutical composition as described or claimed herein. For example, the invention provides a method of making a pharmaceutical composition as described or claimed herein, comprising: (i) making a first liposome type by introducing a first lipid solution of an unsaturated phospholipid, cholesterol, a cationic lipid, docetaxel, and preferably a pegylated phospholipid in ethanol through a first or more port of a multi-port manifold into a mixing chamber and introducing a aqueous solution through a second or more port of the multi-port manifold into the mixing chamber, the liposome formed in the mixing chamber exit the mixing chamber through a third or more exit port, wherein the resulting first liposome type does not comprise doxorubicin; (ii) making a second liposome type by introducing a second lipid solution in ethanol through a first or more inlet port of a multi-port manifold into a mixing chamber and introducing an aqueous solution through a second or more inlet port of the multi-port manifold into the mixing chamber, the liposome formed in the mixing chamber exit the mixing chamber through one or more outlet port. The liposome is then incubated with doxorubicin to encapsulate doxorubicin, wherein the resulting second liposome type does not comprise docetaxel; and (iii) combining predetermined amounts of the first liposome type and the second liposome type, thereby making the pharmaceutical composition as described or claimed herein.

The invention provides a method of treating a subject comprising administering an effective amount of any of the pharmaceutical compositions of the invention described or claimed herein. In various embodiments, the subject has a cancer. In various embodiments, the cancer is a lung cancer, preferably non-small cell lung cancer (NSCLC); colon cancer; breast cancer; or liver cancer, preferably hepatocellular carcinoma (HCC).

These and other advantages of the present technology will be apparent when reference is made to the accompanying drawings and the following description.

Figure 1:
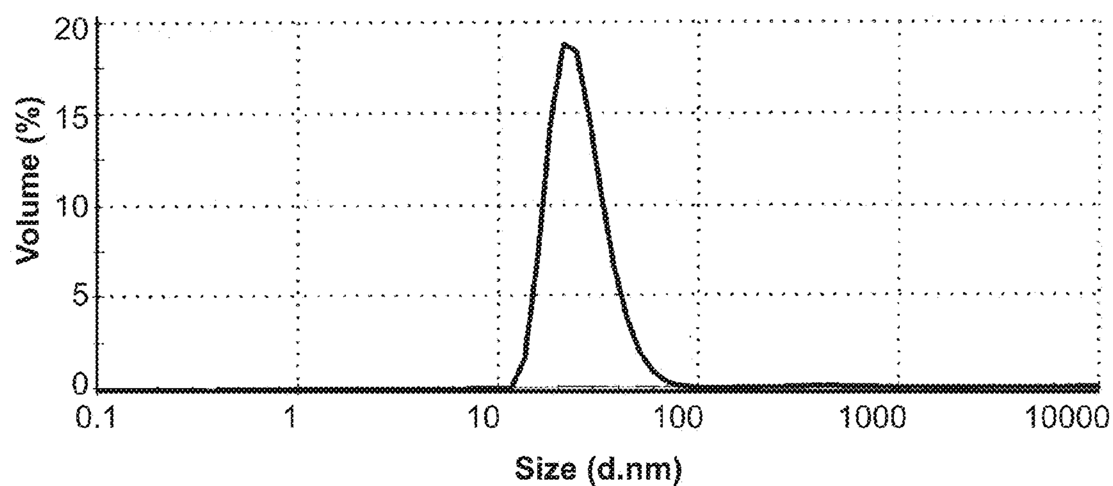
FIG. 1 illustrates volume-weighted particle size distribution of liposomal formulation CPT307A determined by dynamic light scattering.

While the invention comprises embodiments in many different forms, there are shown in the drawings and will herein be described in detail several specific embodiments with the understanding that the present disclosure is to be considered as an exemplification of the principles of the technology and is not intended to limit the invention to the embodiments illustrated.

DETAILED DESCRIPTION

In various aspects and embodiments, the invention provides a pharmaceutical composition including a first liposome type comprising a first API (e.g., docetaxel) and a second liposome type comprising a second API (e.g., doxorubicin). In various embodiments, (i) the first liposome type comprises a first lipid layer comprising an unsaturated phospholipid, cholesterol, and preferably a pegylated phospholipid, and a first active pharmaceutical ingredient (API) (e.g., docetaxel) in the first lipid layer; and (ii) a second liposome type comprising a second lipid layer, an aqueous interior, and a second API (e.g., crystallized doxorubicin) in the aqueous interior. The first liposome type does not comprise the second API (e.g., doxorubicin) and the second liposome type does not comprise the first API (e.g., docetaxel).

As used herein, the phrase "the first liposome type does not comprise the second API and the second liposome type does not comprise the first API" or "the first liposome type does not comprise doxorubicin and the second liposome type does not comprise docetaxel" means that first liposome type includes essentially none, or a negligible amount, of the second API (e.g., doxorubicin) and the second liposome type includes essentially none, or a negligible amount, the first API (e.g., docetaxel). As will be understood by one of ordinary skill in the art, any compound has a partition coefficient between aqueous and non-aqueous phases that are in equilibrium. For example, given a hydrophobic compound (e.g., docetaxel) in a non-aqueous phase (e.g., lipid layer of a liposome) that is in equilibrium with an aqueous phase (e.g., aqueous interior of a liposome), the partition coefficient dictates that some negligible amount (e.g., essentially none) of the hydrophobic compound can be found partitioned to the aqueous phase. In other words, any amount of doxorubicin the first liposome type in the experimental Examples below can be considered as essentially none, or a negligible amount—i.e., the first liposome type does not comprise doxorubicin. Likewise, any amount of docetaxel the second liposome type in the experimental Examples below can be considered as essentially none, or a negligible amount—i.e., the second liposome type does not comprise docetaxel.

The liposomes can be used advantageously to treat a subject, for example, a human subject having cancer. The cancer can be, for example, a lung cancer, preferably non-small cell lung cancer (NSCLC); colon cancer; breast cancer; or liver cancer, preferably hepatocellular carcinoma (HCC). The invention can provide for increased efficacy and/or decreased toxicity, for example relative to (i) other pharmaceutical compositions where the first drug (e.g., docetaxel) and/or the second drug (e.g., doxorubicin) are not in a liposomal formulation. The invention can also provided superior results to known liposomal, and non-liposomal, formulation (e.g., Doxil® and Myocet®, or Taxotere®).

The invention can provide for targeted delivery of both the first and second API, for example to the liver. The invention can mitigate undesired side effects, for example to load a water insoluble drug into the liposome to eliminate the toxic solvent used for the non-liposomal drug (e.g., docetaxel) formulations thus to abolish the toxic solvent induced adverse react. Furthermore, because the first and second API are in separate liposomes, each liposome can be designed specifically for the API it carries. The different combinations of the two liposomal formulations, including different API ratio, different dosing sequence and interval time, can be clinically identified for the treatment of different type of cancers. It also provides physicians a flexibility to adjust the ratios of the two liposomal APIs at patients' bedside to optimize the outcomes while minimizing the adverse reactions for individual patients.

The various features of such liposomes, as well as pharmaceutical compositions including the liposomes and methods of using and making the liposomes are discussed, in turn, below.

Active Pharmaceutical Ingredient (API)

In various aspects and embodiments, the compositions includes a first API (e.g., docetaxel in a first liposome type) and a second API (e.g., doxorubicin in a second, separate, liposome type). While docetaxel and doxorubicin are presented as illustrative examples, other embodiments are possible where a different first API is in the lipid layer of the first liposome type and a different second API is in (e.g., crystallized in) the aqueous interior of the second liposome type.

In various embodiments, the two liposome types can separately include two (or more) anticancer agents, anti-inflammatory agents, anti-diabetic agents, anti-fungal agents, and/or antibiotic agents. Where additional APIs (i.e., more than two) are present, the first and/or second liposome types can include the additional API(s). Alternatively, the additional APIs can be included in liposome(s) separate from the first and second liposome types (e.g., in a third liposome type).

Docetaxel (as generic or under the trade name Taxotere® or Docecad®) is a clinically well-established anti-mitotic chemotherapy medication that works by interfering with cell division. Docetaxel is approved by the FDA for treatment of locally advanced or metastatic breast cancer, head and neck cancer, gastric cancer, hormone-refractory prostate cancer and non small-cell lung cancer. Docetaxel can be used as a single agent or in combination with other chemotherapeutic drugs as indicated depending on specific cancer type and stage.

Docetaxel is a member of the taxane drug class, which also includes the chemotherapeutic medication paclitaxel. Accordingly, in some embodiments, docetaxel can be substituted for another taxane that can be disposed within the lipid layer of the liposome.

The optimal dose scheduling of taxanes remains unconfirmed, but most studies find significant mortality benefit following either a three-week or a one-week administration schedule. While some research suggests weekly administration as an optimal schedule, the official docetaxel package insert recommends administration every three weeks. Important toxicities to note include neutropenia, febrile neutropenia and neurosensory disturbances. Such toxicities have been well documented in Phase II and Phase III clinical trials and can be anticipated and subsequently managed.

In various embodiments, the invention can increase the efficacy of, and/or decrease undesired side effects from, the docetaxel.

Doxorubicin (trade name Adriamycin®; pegylated liposomal form trade name Doxil®; nonpegylated liposomal form trade name Myocet®), also known as hydroxydaunorubicin and hydroxydaunomycin, is a drug used in cancer chemotherapy and derived by chemical semisynthesis from a bacterial species. It is an anthracycline antibiotic (note: in this context, this does not mean it is used to treat bacterial infections) closely related to the natural product daunomycin and like all anthracyclines, it is believed to work by intercalating DNA, with the most serious adverse effect being life-threatening heart damage. It is commonly used in the treatment of a wide range of cancers, including hematological malignancies (blood cancers, like leukaemia and lymphoma), many types of carcinoma (solid tumors) and soft tissue sarcomas. It is often used in combination chemotherapy as a component of various chemotherapy regimens. In some embodiments, doxorubicin can be substituted for another anthracycline or another anticancer agent that can be disposed within the aqueous interior of the liposome.

Common adverse effects of doxorubicin include hair loss (seen in most of those treated with the drug), myelosuppression (a compromised ability of the body's bone marrow to produce new blood cells), nausea and vomiting (which are seen in roughly 30-90% of people treated with the drug), oral mucositis, oesophagitis, diarrhea, skin reactions (including hand-foot syndrome) and localized swelling and redness along the vein in which the drug is delivered. Less common, yet serious reactions include hypersensitivity reactions (including anaphylaxis), radiation recall, heart damage and liver dysfunction.

The drug is administered intravenously, as the hydrochloride salt. It is sold under a number of different brand names, including Adriamycin® PFS, Adriamycin® RDF, or Rubex®. Doxorubicin is photosensitive, and containers are often covered by an aluminum bag and/or brown wax paper to prevent light from affecting it. Doxorubicin is also available in liposome-encapsulated forms as Doxil® (pegylated form), Myocet® (nonpegylated form), and Caelyx®, although these forms must also be given by intravenous injection.

In various embodiments, the invention can increase the efficacy of and/or decrease undesired side effects from, the doxorubicin.

In some embodiments, the API may be a polynucleotide (including an oligonucleotide) a protein or a small molecule.

In one embodiment the API is a polynucleotide. The polynucleotide may be a genomic DNA fragment, cDNA, mRNA, ssRNA, dsRNA, microRNA, siRNA, shRNA, sdRNA, DsiRNA, LNA, and antisense DNA or RNA.

Alternatively, the API may be a small molecule drug. Preferably, the molecule has a molecular weight from about 1500 g/mole to about 50 g/mole.

An API can include, for example, two or more of the following: an anticancer agent, an antibiotic agent, an antiviral agent, an anti-fungal agent, or an analgesic.

Exemplary anticancer agents may include but are not limited acivicin, aclarubicin, acodazole, ametantrone, aminoglutethimide, anthramycin, asparaginase, azacitidine, azetepa, bisantrene, bleomycin, busulfan, cactinomycin, calusterone, caracemide, carboplatin, carfilzomib, carmustine, carubicin, chlorambucil, cisplatin, cyclophosphamide, cytarabine, dacarbazine, dactinomycin, daunorubicin, dezaguanine, diaziquone, docetaxel, doxorubicin, epipropidine, erlotinib, etoposide, etoprine, floxuridine, fludarabine, fluorouracil, fluorocitabine, hydroxyurea, iproplatin, leuprolide acetate, lomustine, mechlorethamine, megestrol acetate, melengestrol acetate, mercaptopurine, methotrexate, metoprine, mitocromin, mitogillin, mitomycin, mitosper, mitoxantrone, mycophenolic acid, nocodazole, nogalamycin, oxisuran, paclitaxel, peliomycin, pentamustine, porfiromycin, prednimustine, procarbazine hydrochloride, puromycin, pyrazofurin, riboprine, semustine, sparsomycin, spirogermanium, spiromustine, spiroplatin, streptozocin, talisomycin, tegafur, teniposide, teroxirone, thiamiprine, thioguanine, tiazofurin, triciribine phosphate, triethylenemelamine, trimetrexate, uracil mustard, uredepa, vinblastine, vincristine, vindesine, vinepidine, vinrosidine, vinzolidine, zinostatin and zorubicin.

In specific embodiments, the anti-cancer agent is chosen from carfilzomib, daunorubicin, doxorubicin, paclitaxel, docetaxel, cisplatin, carboplatin, cytarabine, floxuridine, fludarabine, fluorouracil, iproplatin, leuprolide acetate, and methotrexate.

Exemplary antibiotic agents may include but are not limited to aminoglycoside; amikacin; gentamicin; kanamycin; neomycin; netilmicin; steptomycin; tobramycin; ansamycins; geldanamycin; herbimycin; carbacephem; loracarbef; carbacepenem; ertapenem; doripenem; imipenem/cilastatin; meropenem; cephalosporin; cefadroxil; cefazolin; cefalotin or cefalothin; cefalexin; cefaclor; cefamandole; cefoxitin; cefprozil; cefuroxime; cefixime; cefdinir; cefditoren; cefoperazone; cefotaxime; cefpodoxime; ceftazidime; ceftibuten; ceftizoxime; ceftriaxone; cefepime; ceftobiprole; glycopeptide; teicoplanin; vancomycin; macrolides; azithromycin; clarithromycin; dirithromycin; erythromicin; roxithromycin; troleandomycin; telithromycin; spectinomycin; monobactam; aztreonam; penicillins; amoxicillin; ampicillin; azlocillin; carbenicillin; cloxacillin; dicloxacillin; flucloxacillin; mezlocillin; meticillin; nafcillin; oxacillin; penicillin, piperacillin, ticarcillin; bacitracin; colistin; polymyxin B; quinolone; ciprofloxacin; enoxacin; gatifloxacin; levofloxacin; lomefloxacin; moxifloxacin; norfloxacin; ofloxacin; trovafloxacin; sulfonamide; mafenide; prontosil (archaic); sulfacetamide; sulfamethizole; sufanilimide (archaic); sulfasalazine; sulfisoxazole; trimethoprim; trimethoprim-sulfamethoxazole (co-trimoxazole) (TMP-SMX); tetracycline; demeclocycline; doxycycline; minocycline; oxytetracycline; tetracycline; arsphenamine; chloramphenicol; clindamycin; lincomycin; ethambutol; fosfomycin; fusidic acid; furazolidone; isoniazid; linezolid; metronidazole; mupirocin; nitrofuantoin; platensimycin; polymyxin, purazinamide; quinupristin/dalfopristin; rifampin or rifampicin; and timidazole.

Exemplary antiviral agents may include, but are not limited to thiosemicarbazone; metisazone; nucleoside and/or nucleotide; acyclovir; idoxuridine; vidarabine; ribavirin; ganciclovir; famciclovir; valaciclovir; cidofovir; penciclovir; valganciclovir; brivudine; ribavirin, cyclic amines; rimantadine; tromantadine; phosphonic acid derivative; foscamet; fosfonet; protease inhibitor; saquinavir; indinavir; ritonavir; nelfinavir; amprenavir; lopinavir; fosamprenavir; atazanavir; tipranavir; nucleoside and nucleotide reverse transcriptase inhibitor; zidovudine; didanosine; zalcitabine; stavudine; lamivudine; abacavir; tenofovir disoproxil; adefovir dipivoxil; emtricitabine; entecavir; non-nucleoside reverse transcriptase inhibitor; nevirapine; delavirdine; efavirenz; neuraminidase inhibitor; zanamivir; oseltamivir; moroxydine; inosine pranobex; pleconaril; and enfuvirtide.

Exemplary anti-fungal agents may include but are not limited to allylamine; terbinafine; antimetabolite; flucytosine; azole; fluconazole; itraconazole; ketoconazole; ravuconazole; posaconazole; voriconazole; glucan synthesis inhibitor; caspofungin; micafungin; anidulafungin; polyenes; amphotericin B; amphotericin B Colloidal Dispersion (ABCD); and griseofulvin.

Exemplary analgesics may include, but are not limited to opiate derivative, codeine, meperidine, methadone, and morphine.

In various embodiments, docetaxel is the only API in the first liposome type and/or doxorubicin is the only API in the second liposome type.

In various embodiments, the molar ratio of the first lipid layer components:doxorubicin is about 100:1 to about 5:1, preferably about 20:1 to about 10:1; and the molar ratio of the second lipid layer components:docetaxel is about 100:1 to about 5:1, preferably about 20:1 to about 10:1.

In various embodiments, the molar ratio of second API (e.g., doxorubicin):first API (e.g., docetaxel) is about 10:1 to 1:10, preferably about 5:1 to 1:5, and more preferably about 3:1 to 1:3.

The Lipid Layer and Aqueous Solutions

The invention utilizes lipid and aqueous solutions, for example in making liposomes in accordance with the invention. Accordingly, the composition lipid and/or aqueous solutions can affect the final composition of the liposomes.

In various embodiments, the lipid solution may comprise an organic solvent. The organic solvent may be a water miscible solvent. Preferably, the water miscible solvent is selected from the group consisting of ethanol, methanol, DMSO and isopropanol. Most preferably, the organic solvent is ethanol.

As used herein the term of "cationic lipid" refers to a lipid or a cholesterol derivative that carries a net positive charge at about pH 3-pH 9.

As used herein the term of "anionic lipid" refers to a lipid or a cholesterol derivative that carries a net negative charge at about pH 3-pH 9.

As used herein the term "pegylated lipid" refers to a lipid that is conjugated with a polyethylene glycol polymer.

As used herein the term "neutral lipid" refers to the lipid that does not carry net charge at about pH 3-pH 9.

The lipid solution may include a mixture of lipids. The mixture of lipids preferably includes cholesterol.

The mixture of lipids may also include a cationic lipid. The cationic lipid may be, but is not limited to, N,N-dioleyl-N,N-dimethylammonium chloride ("DODAC"); N-(2,3-dioleyloxy)propyl)-N,N,N-trimethylammonium chloride ("DOTMA"); N-(2,3-dioleyloxy)propyl)-N,N-dimethylammonium chloride ("DODMA"); N,N-distearyl-N,N-dimethylammonium bromide ("DDAB"); N-(2,3-dioleoyloxy)propyl)-N,N,N-trimethylammonium chloride ("DOTAP"); N-(2,3-dioleoyloxy)propyl)-N,N-dimethylammonium chloride ("DODAP"); 3-(N—(N',N'-dimethylaminoethane)carbamoyl)cholesterol ("DC-Chol"); N-(1,2-dimyristyloxyprop-3-yl)-N,N-dimethyl-N-hydroxyethyl ammonium bromide ("DMRIE"); 1.2-dilinoleyloxy-N,N-dimethyl-3-aminopropane (DLinDMA); 1,2-distearyloxy-N,N-dimethyl-3-aminopropane (DSDMA); 1.2-dilinolenyloxy-N,N-dimethyl-3-aminopropane (DLenDMA); 2-{4-[(3b)-cholest-5-en-3-yloxy]butoxy}-N,N-dimethyl-3-[(9Z,12Z)-octadeca-9,12-dien-1-yloxy]propan-amine (CLinDMA).

In some embodiments the mixture of lipids may include an anionic lipid. The anionic lipid may be but is not limited to diacylglycerol phophatidic acid (1,2-distearoyl-sn-glycero-3-phosphate (DSPA); 1,2-dipalmitoyl-sn-glycero-3-phosphate (DPPA); 1,2-dimyristoyl-sn-glycero-3-phosphate (DMPA); 1,2-dilauroyl-sn-glycero-3-phosphate (DLPA); 1,2-dioleoyl-sn-glycero-3-phosphate (DOPA)), diacylglycerol phosphoglycerol (1,2-distearoyl-sn-glycero-3-phospho-(1'-rac-glycerol) (DSPG); 1,2-dipalmitoyl-sn-glycero-3-phospho-(1'-rac-glycerol) (DPPG); 1,2-dimyristoyl-sn-glycero-3-phospho-(1'-rac-glycerol) (DMPG); 1,2-dilauroyl-sn-glycero-3-phospho-(1'-rac-glycerol) (DLPG); 1,2-dioleoyl-sn-glycero-3-phospho-(1'-rac-glycerol) (DOPG)), phosphatidylglycerol, cardiolipin, diacylphosphatidylserine, N-succinyl phosphatidylethanolamines, N-glutarylphosphatidylethanolamines, lysylphosphatidylglycerols, and other anionic modifying groups joined to neutral lipids. The mixture of lipids may also include a neutral lipid. The neutral lipid may be but is not limited to diacylglycerol phosphocholine (L-α-phosphatidylcholine, hydrogenated (Soy) (HSPC); diacylglycerol phosphocholine (L-α-phosphatidylcholine, (Soy) (Soy PC) 1,2-distearoyl-sn-glycero-3-phosphocholine (DSPC); 1,2-dipalmitoyl-sn-glycero-3-phosphocholine (DPPC); 1,2-dimyristoyl-sn-glycero-3-phosphocholine (DMPC); 1,2-dilauroyl-sn-glycero-3-phosphocholine (DLPC); 1,2-dioleoyl-sn-glycero-3-phosphocholine (DOPC), diacylglycerol phosphoethanolamine (1,2-distearoyl-sn-glycero-3-phosphoethanolamine (DSPE); 1,2-dipalmitoyl-sn-glycero-3-phosphoethanolamine (DPPE); 1,2-dimyristoyl-sn-glycero-3-phosphoethanolamine (DMPE); 1,2-dilauroyl-sn-glycero-3-phosphoethanolamine (DLPE); 1,2-dioleoyl-sn-glycero-3-phosphoethanolamine (DOPE), and phosphatidylserine.

The mixture of lipids may also include a pegylated lipid. The pegylated lipid may be but is not limited to 1,2-distearoyl-sn-glycero-3-phosphoethanolamine-N-[methoxy (polyethylene glycol)-2000] (mPEG-2000-DSPE); 1,2-dioctadecanoyl-sn-glycero-3-phosphoethanolamine-N-[methoxy(polyethylene glycol)-2000] (mPEG-2000-DOPE); 1,2-dipalmitoyl-sn-glycero-3-phosphoethanolamine-N-[methoxy(polyethylene glycol)-2000] (mPEG-2000-DPPE); 1,2-dimyristoyl-sn-glycero-3-phosphoethanolamine-N-[methoxy(polyethylene glycol)-2000] (mPEG-2000-DMPE); 1,2-dilauroyl-sn-glycero-3-phosphoethanolamine-N-[methoxy(polyethylene glycol)-2000] (mPEG-2000-DLPE); 1,2-distearoyl-sn-glycero-3-phosphoethanolamine-N-[methoxy(polyethylene glycol)-5000] (mPEG-5000-DSPE); 1,2-dioctadecanoyl-sn-glycero-3-phosphoethanolamine-N-[methoxy(polyethylene glycol)-5000] (mPEG-5000-DOPE); 1,2-dipalmitoyl-sn-glycero-3-phosphoethanolamine-N-[methoxy(polyethylene glycol)-5000] (mPEG-5000-DPPE); 1,2-dimyristoyl-sn-glycero-3-phosphoethanolamine-N-[methoxy(polyethylene glycol)-5000] (mPEG-5000-DMPE); 1,2-dilauroyl-sn-glycero-3-phosphoethanolamine-N-[methoxy(polyethylene glycol)-5000] (mPEG-5000-DLPE).

The mixture of lipid may also include a lipid-like molecule or lipidoid. The mixture of lipid may also include a lipid- or cholesterol-conjugated molecule including a protein, or a peptide, or an oligonucleotide.

In various embodiments, the lipid layer includes one or more of the lipid components disclosed herein.

In various embodiments, the first lipid layer and/or the second lipid layer consist of unsaturated phospholipid and cholesterol.

In various embodiments, the first lipid layer and/or the second lipid layer consist of unsaturated phospholipid, cholesterol, and pegylated phospholipid.

In various embodiments, the first lipid layer and the second lipid layer comprise different lipid compositions (e.g., different lipid components and/or different amounts of certain lipid components). In various embodiments, the first liposome and the second liposome are different (e.g., in addition to comprising different APIs, derived from different lipid solutions and/or aqueous solutions as described below). Alternatively, in some embodiments, the first and second lipid layers are essentially the same (e.g., other than comprising different APIs, comprising essentially the same lipid components and amounts thereof).

In various embodiments, the first lipid layer, the second lipid layer, or both the first and second lipid layers comprise: about 20-75%, preferably about 30-60%, (molar) unsaturated phospholipid; about 10-60%, preferably 20-50%, (molar) cholesterol; and about 0-20%, preferably 1-10%, (molar) pegylated phospholipid.

In various embodiments, the molar ratio of the lipid layer components:doxorubicin is about 100:1 to about 5:1, preferably about 20:1 to about 10:1; and the molar ratio of the lipid layer components:docetaxel is about 100:1 to about 5:1, preferably about 20:1 to about 10:1.

In various embodiments, the molar ratio of doxorubicin: docetaxel is about 10:1 to 1:10, preferably about 5:1 to 1:5, and more preferably about 3:1 to 1:3.

In various embodiments, the unsaturated phospholipid comprises a polyunsaturated phospholipid or a monounsaturated phospholipid, preferably a phosphatidylcholine, and more preferably and soy phosphatidylcholine or 1,2-dioleoyl-sn-glycero-3-phosphatidylcholine (DOPC).

In various embodiments, the cholesterol comprises a cholesterol derivative, preferably a cationic cholesterol derivative, more preferably an amino cholesterol derivative, and still more preferably dimethylaminoethanecarbamoyl-cholesterol (DC-cholesterol).

In various embodiments, the pegylated phospholipid comprises a phosphoethanolamine, preferably a 1,2-distearoyl-sn-glycero-3-phosphoethanolamine (DSPE) and wherein the pegylation is a PEG 500 to PEG 3000, preferably PEG 2000.

In various embodiments, the composition of the lipid layer is tuned to achieve a desired loading of the first drug. Although at least a fraction of the first drug is in the lipid layer, one of ordinary skill will understand that the first drug will have a partition coefficient between the lipid layer and aqueous interior. In some embodiments, essentially all of the first drug will be in the lipid layer.

The aqueous solution of the process preferably includes water and a buffer. Buffers may be of but are not limited to phosphate, histidine, HEPES, Tris, acetate, carbonate, and citrate. In various embodiments, the composition of the aqueous solution is tuned to achieve a desired loading (and/or crystallization) of the second drug. Although at least a fraction of the second drug is in the aqueous interior of the liposome, one of ordinary skill will understand that the second drug will have a partition coefficient between the lipid layer and aqueous interior. In some embodiments, essentially all of the second drug will be in the aqueous interior.

Although, in some embodiments, the first lipid layer and the second lipid layer have essentially the same lipid compositions, one skilled in the art will appreciate that, in other embodiments, the first lipid layer and the second lipid layer can have different lipid compositions (e.g., different lipid components and/or different amounts of certain lipid components).

Methods for Making Liposomes

Examples of apparatuses and methods that can be adapted for making the liposomes of the invention can be found, for example, in U.S. patent application Ser. No. 14/209,187 (and published as US20140348900), which is herein incorporated by reference in its entirety. A description of a number of different methods of making liposomes in accordance with the invention are presented in the Examples below.

The invention also provides a method of making the pharmaceutical composition as described or claimed herein. For example, the invention provides a method of making a pharmaceutical composition as described or claimed herein, comprising: (i) making a first liposome type by introducing a first lipid solution of an unsaturated phospholipid, a sterol, docetaxel, and preferably a pegylated phospholipid in ethanol through a first port into a mixing chamber and introducing a first aqueous solution through a second port into the mixing chamber, wherein the resulting first liposome type does not comprise doxorubicin; (ii) making a second liposome type by introducing a second lipid solution in ethanol through a first port into a mixing chamber and introducing a second aqueous solution through a second port into the mixing chamber and incubating the resulting liposomes with doxorubicin, wherein the resulting second liposome type does not comprise docetaxel; and (iii) combining predetermined amounts of the first liposome type and the second liposome type, thereby making the pharmaceutical composition as described or claimed herein.

In various embodiments, the angle between at least one lipid and at one aqueous solution inlet ports is not 180° or a substantially similar angle. In some aspects, at least one stream of lipid solution and at one stream of aqueous solution collide at an angle less than about 180°. Thus, in some aspects, the method does not include a T-connector.

In some embodiments, the angle between at least one lipid and at one aqueous solution inlet ports is about 120° or less, e.g., 115° or less, 100° or less, 90° or less, 80° or less, 72° or less, 60° or less, 45° or less, 30° or less, 18° or less, In some embodiments, the aqueous solution in step ii) is introduced via at least two inlet ports, e.g., at least 3, 4, 5, 6, 7, 8, 9, 10, 11, 12, 13, 14, 15, 16, 17, 18, 19, 20 or more. In some embodiments, the aqueous solution in step ii) is introduced via at least 3 but no more than 11 inlet ports, e.g., at least 3 but not more than 7, at least 3 but no more than 5, at least 4 but no more than 11, at least 5 but no more than 11, at least 6 but no more than 11.

In some embodiments, at least two (e.g., 3, 4, 5, 6, 7, etc.) aqueous inlet ports and at least one (e.g., 2, 3, 4, 5, etc.) lipid solution inlet port are in the same plane.

In some embodiments, at least one (e.g., 2) outlet port is substantially perpendicular to the plane of inlet ports. In other embodiments, at least one (e.g., 2, 3, 4, 5, etc.) outlet port is substantially not perpendicular to the plane of inlet ports.

In some embodiments, at least two (e.g., 3, 4, 5, 6, 7, etc.) aqueous solution inlet ports and at least one (e.g., 2, 3, 4, 5, etc.) lipid solution inlet port are not in the same plane.

Preparing Lipid Solutions

The lipid solution may be made from the stock solutions of individual lipids that are mixed together. Lipids are preferably dissolved in an organic solvent to make a lipid solution. The organic solvent used for making the lipid solution may be miscible with water. Preferably the solvent may ethanol, methanol, DMSO, propanol, DMF, THF, acetone, dioxane, ethylene glycol, polyethylene glycol and isopropanol. More preferably, the solvent is polyethylene glycol, isopropanol, and ethanol. Preferably, the solvent includes less than 10% water. In some cases, the lipid solution may be made from a mixture of lipids, thereupon dissolving the mixture in an organic solvent. The concentration of the total lipids in the solution may be in the range from about 1 mg/mL to about 200 mg/mL, e.g., from about 1 mg/mL to about 100 mg/mL. More preferably, the concentration of the total lipids in the solution may be in the range from about 5 mg/mL to about 100 mg/mL or form about 10 mg/mL to 100 mg/mL. In some embodiments, the organic solvent is ethanol at a concentration of about 70% or more (e.g., 75% or more, 80% or more, 85% or more, 90% or more, 95% or more, 100%).

The mixture of lipids will be optimized as required for optimal delivery of the API and is readily optimized by routine experimentation by one of ordinary skill in the art.

In certain embodiments, a water-insoluble API may be dissolved in the lipid solution. The concentration of the API in the lipid solution will depend on the efficacy of the agent and may easily be determined by one of ordinary skill in the art. The lipid/API ratio will determined by the encapsulation power of the liposome to the API.

Preparing Aqueous Solutions

A water-soluble API component may be dissolved in a first aqueous solution (S1). The pH and salinity of the solution may be optimized to accommodate the requirements for the interaction between the API component and the lipids to form liposome. These conditions may be readily determined by one of ordinary skill in the art. Samples are provided in the Examples below. As will be readily apparent to those of skill in the art, an aqueous solution that lacks an API, referred to as (S2), may be similar to a solution having the agent. Alternatively, S1 and S2 may be different.

Liposome Preparation, Mixing the Solutions

The lipid solution and the aqueous solution(s) preferably enter the manifold from different ports, each with a flow rate of from about 1 mL/min to about 6000 mL/min. Preferably, the flow rates may be from about 5 mL/min to about 1000 mL/min. More preferably, the rates may be from about 20 mL/min to about 600 mL/min. In some embodiments, the flow rates are adjusted based on the size of inlet ports to obtain the desired liposome size, morphology, PDI, and manufacturing scales.

As described above, the first liposome and the second liposome can be different (e.g., different lipid components and/or different amounts of certain lipid components, different aqueous interiors, etc.). In such cases, the first and second liposomes can be made from different lipid solutions and/or aqueous solutions. However, one skilled in the art will appreciate that in some embodiments, the first and second lipid layers can be essentially the same.

In some embodiments, the lipid solution and/or the aqueous solution is introduced via port size of 0.1-5 mm at a flow rate about 1 mL/min to about 2,500 mL/min.

In some embodiments, the flow velocity of the lipid solution and/or the aqueous solution is from about 0.02 m/s to about 40 m/s, e.g., from 0.1 m/s to 30 m/s, from 0.2 m/s to 20 m/s. The flow velocity is adjusted based on the size of inlet ports to obtain the desired liposome size, morphology, PDI, and manufacturing scale.

Loading of the API into Liposome

In the mixing chamber the lipids are believed to instantaneously assemble into liposome particles. When the drug API is carried by the lipid solution or by aqueous solution, it may be encapsulated in the liposome by either lipophilic or electrostatic interaction, or both, between the API and the lipids.

The present invention also provides a method of producing liposome that do not contain an API (so-called "empty" liposome). In such embodiments, the API is absent from both the lipid solution and the aqueous solution that are mixed in the manifold. The API may be loaded into the liposomes by the process of diffusion or another process. For example, doxorubicin may be loaded into the liposome with a pH gradient. See U.S. patent application Ser. No. 10/019, 200, PCT Publication No. WO 2001/005373, U.S. Pat. Nos. 5,785,987, 5,380,531, 5,316,771, and 5,192,549, all of which are incorporated herein by reference.

Preferably, the API is mixed with a liposome solution to upload the API into the liposome by diffusion. In one aspect, the API is dissolved in an aqueous solution, and the solution is mixed with the empty liposome. In another aspect, the API may be readily soluble in the solution of empty liposome, and therefore, the API may be directly mixed with the solution of the empty liposome.

The volume ratio of the solution of the API to the empty liposome solution of the API is preferably in the range from about 1:50 to about 1:5. A lower volume of the solution is preferred because it avoids a significant dilution to the final liposome solution.

The drug encapsulation efficiency is preferably greater than 70%. More preferably the efficiency is greater than 80%. Most preferably, the efficiency is greater than 90%.

Liposome Concentration Adjustment

Tangent flow filtration may be used to concentrate the liposome solution.

Buffer Change

Residual organic solvent in the liposome solution may be removed by a buffer change. Preferably, the buffer change is performed by tangent flow filtration. In another embodiment, the buffer change may be performed by dialysis.

Sterile Filtration

The liposome solutions can be sterilized, for example, by passing the solution through a 0.22 micron sterile filter.

Liposomes

In various embodiments, the Z-average particle size of the liposomes is from about 10 nm to about 2,000 nm, preferably less than 300 nm, more preferably, the mean particle size may be about 10 to 300 nm or about 20 to about 300 nm. Most preferably, the mean particle size is about 20 to 120 nm In some embodiments, the liposomes have a polydispersity index from about 0.005 to about 0.8, e.g., 0.005 to about 0.5, 0.01 to about 0.5, 0.01 to about 0.4, 0.01 to about 0.2.

Preferably, more than 70% of API is encapsulated in the liposomes. More preferably, more than 80% of API is encapsulated in the liposomes, most preferably, more than 90% of API is encapsulated in the liposomes.

Optionally, liposomes can be unilamellar. Alternatively, the liposomes can be of multilamellar, or of inverted hexagonal or cubic morphology, or as lipid discs, or hollow liposomes.

Pharmaceutical Compositions

In various embodiments, the pharmaceutical composition is for use as a medicament. In various embodiments, the pharmaceutical composition is for use as a cancer therapeutic. In various embodiments, the pharmaceutical composition comprises an antibiotic, antiviral, anti-diabetes, anti-hypertension, anti-fungal, or analgesic drug.

The invention also provides a pharmaceutical composition consisting of: (i) a plurality of liposomes of the first type as described or claimed herein; (ii) a plurality of liposomes of the second type as described or claimed herein; and (iii) one or more pharmaceutical excipients.

In various embodiments, the plurality of liposomes are comprised in an injectable formulation, for example, by subcutaneous, intravenous, intramuscular, intrathecal or intraperitoneal injection. Injectable formulations can be aqueous solutions, preferably in physiologically compatible buffers such as Hanks' solution, Ringer's solution, or physiological saline buffer. The injectable formulation can contain formulatory agents such as suspending, stabilizing and/or dispersing agents. Alternatively, the liposomes can be in a dried or powder form for constitution with a suitable vehicle, e.g., sterile pyrogen-free water, before use.

Treatment and Administration

The invention provides a method of treating a subject comprising administering an effective amount of any of the pharmaceutical compositions of the invention described or claimed herein. In various embodiments, the subject has a cancer. In various embodiments, the cancer is a lung cancer, preferably non-small cell lung cancer (NSCLC); colon cancer; breast cancer; or liver cancer, preferably hepatocellular carcinoma (HCC).

Accordingly, the invention provides methods for treating cancer cells and/or tissue, including cancer cells and/or tissue in a human subject. Cancer can be caused by malignant tumors formed by an abnormal growth of cells and tissue leading to organ failure.

Solid tumors can be neoplasms (new growth of cells) or lesions (damage of anatomic structures or disturbance of physiological functions) formed by an abnormal growth of body tissue cells other than blood, bone marrow or lymphatic cells. A solid tumor consists of an abnormal mass of cells which may stem from different tissue types such as liver, colon, breast, or lung, and which initially grows in the organ of its cellular origin. However, such cancers may spread to other organs through metastatic tumor growth in advanced stages of the disease.

The subject being treated may have been diagnosed with cancer. The subject may have locally advanced, unresectable, or metastatic cancer and/or may have failed a prior first-line therapy. In various embodiments, the cancer is liver cancer (e.g., hepatocellular carcinoma, HCC). In various embodiments, the liver cancer (e.g., HCC) can be intermediate, advanced, or terminal stage. The liver cancer (e.g., HCC) can be metastatic or non-metastatic. Liver cancer can include a liver tumor resulting from the metastasis of a non-liver cancer, to the liver. The liver cancer (e.g., HCC) can be resectable or unresectable. The liver cancer (e.g., HCC) can comprise a single tumor, multiple tumors, or a poorly defined tumor with an infiltrative growth pattern (into portal veins or hepatic veins). The liver cancer (e.g., HCC) can comprise a fibrolamellar, pseudoglandular (adenoid), pleomorphic (giant cell), or clear cell pattern. The liver cancer (e.g., HCC) can comprise a well differentiated form, and tumor cells resemble hepatocytes, form trabeculae, cords, and nests, and/or contain bile pigment in cytoplasm. The liver cancer (e.g., HCC) can comprise a poorly differentiated form, and malignant epithelial cells are discohesive, pleomorphic, anaplastic, and/or giant. In some embodiments, the liver cancer (e.g., HCC) is associated with hepatitis B, hepatitis C, cirrhosis, or type 2 diabetes.

In various embodiments, the cancer is a lung cancer, preferably non-small cell lung cancer (NSCLC); colon cancer; breast cancer; or liver cancer, preferably hepatocellular carcinoma (HCC).

In various embodiments, the docetaxel can be in a concentration of 10, 20, 30, 40, 50, 75, 80, 100, 125, 150, or 160 mg/mL. A dose can be about 10 mg/m$^2$ to 150 mg/m$^2$ (e.g., 10, 20, 25, 30, 40, 50, 60, 70, 75, 80, 90, 100, 110, 120, 125, 130, 140, or 150 mg/m$^2$). For example, a dose can be 75 mg/m$^2$. A dose can be administered every 3 weeks for 1, 2, 3, 5, 5, or 6 cycles. One skilled in the art will appreciate that dosing guidelines for docetaxel are known in the art, and can be adapted based upon factors including, but not limited to the cancer type, the cancer stage, the dosing regimen, the dose of doxorubicin, and/or the efficacy of the pharmaceutical compositions of the invention.

In various embodiments, the doxorubicin can be in a concentration of 0.1, 0.5, 1, 1.5, 2, 3, 4, or 5 mg/mL. A dose can be about 1 mg/m$^2$ to 100 mg/m$^2$ (e.g., 1, 2, 3, 4, 5, 6, 7, 8, 9, 10, 20, 25, 30, 40, 50, 60, 70, 75, 80, 90, or 100 mg/m$^2$). For example, a dose can be 30 mg/m$^2$. A dose can be administered every 3 weeks for 1, 2, 3, 5, 5, or 6 cycles. One skilled in the art will appreciate that dosing guidelines for docetaxel are known in the art, and can be adapted based upon factors including, but not limited to the cancer type, the cancer stage, the dosing regimen, the dose of doxorubicin, and/or the efficacy of the pharmaceutical compositions of the invention.

In various embodiments, the liposome of the first API (e.g. docetaxel) and the liposome of the second API (e.g. doxorubicin) are mixed and co-administered to a subject.

In various embodiments, the liposome of the first API (e.g. docetaxel) and the liposome of the second API (e.g. doxorubicin) are administered separately in sequence.

The following examples are illustrative and not restrictive. Many variations of the technology will become apparent to those of skill in the art upon review of this disclosure. The scope of the technology should, therefore, be determined not with reference to the examples, but instead should be determined with reference to the appended claims along with their full scope of equivalents.

EXAMPLES

Example 1: Preparation of Liposomal formulation CPT307A

CPT307A comprises a nonsaturated lipid 1,2-Dioleoyl-sn-glycero-3-Phosphatidylcholine (DOPC), cholesterol, and 1,2-distearoyl-sn-glycero-3-phosphoethanolamine-N-[methoxy9polyethyleneglycol)-2000]. A lipid solution in ethanol was made by dissolving 1200 mg of 1,2-Dioleoyl-sn-glycero-3-Phosphatidylcholine (DOPC), 160 mg of cholesterol, and 400 mg of 1,2-distearoyl-sn-glycero-3-phosphoethanolamine-N-[methoxy9polyethyleneglycol)-2000] (mPEG2000-DSPE) in 40 mL of anhydrous ethanol. In addition, three aqueous solutions of 250 mM ammonium sulfate, pH 6.5 were used. Twenty milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass bottle and was then concentrated by tangent flow filtration. The buffer was changed into a histidine/sucrose buffer (10 mM histidine, 9.2% sucrose, pH 6.5) by tangent flow filtration.

Liposomal formulation CPT307A was prepared by loading doxorubicin (DXR) into the empty liposomes. Twenty eight milliliters of the empty liposomes was mixed with 6.85 mL of a DXR solution in the histidine/sucrose buffer at a concentration of 8.93 mg/mL, and incubated at 42° C. for 3 hours, 99.8% of DXR was encapsulated. The encapsulated liposome was then sterilized by filtration through a 0.22 μm filter. The composition (% molar) of the CPT307A lipid solution is illustrated in Table 1. The final Z-average particle size of the loaded liposome was 37.9 nm, with a DXR concentration of 1.74 mg/mL. The volume-weighted particle size distribution of CPT307A determined by dynamic light scattering (Malvern Zetasizer Nano ZS) is shown in FIG. 1.

TABLE 1

Lipid Composition of Example 1.

| Component | CPT307A % (molar) * |
|---|---|
| DOPC | 73.6 |
| Cholesterol | 20 |
| mPEG2000-DSPE | 6.4 |
| DXR | 13.1 |

* The value represents the molar % of each component vs. total lipids.

Example 2: Preparation of Liposomal Formulation CPT307B

Figure 2:
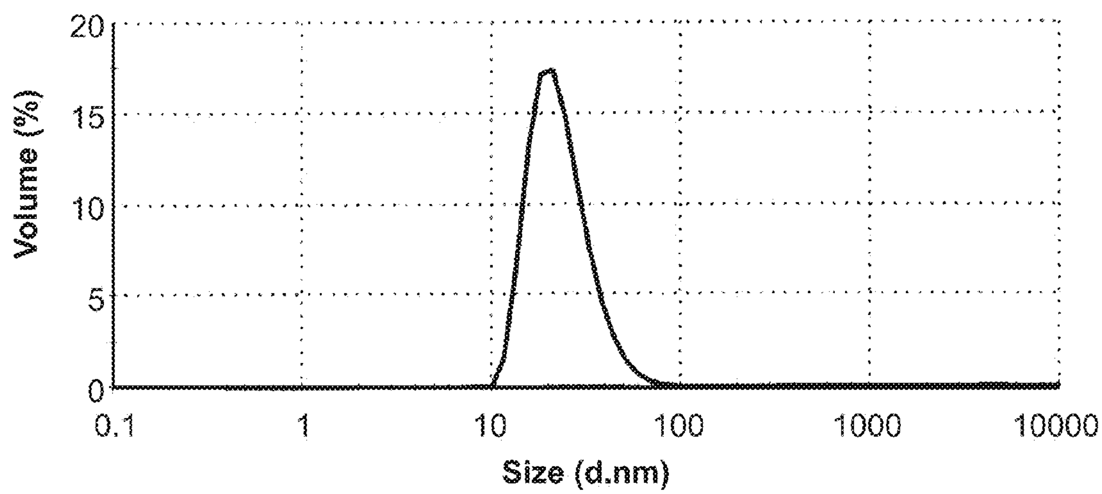
FIG. 2 illustrates volume-weighted particle size distribution of liposomal formulation CPT307B determined by dynamic light scattering.

The lipid composition of CPT307B is identical to CPT307A, it comprises DOPC, cholesterol, and mPEG2000-DSPE. It was found that compared to a saturated lipid such as DSPC, DPPC, HSPC, the nonsaturated lipid DOPC makes liposome a greater capacity to encapsulate docetaxel. To make CPT307B, a lipid/DOCE solution was prepared by dissolving 2100 mg of DOPC, 280 mg of cholesterol, 700 mg of mPEG2000-DSPE, and 175 mg of docetaxel (DOCE) in 70 mL of anhydrous ethanol. The composition (% molar) of the CPT307B lipid solution is illustrated in Table 2. In addition, three aqueous solutions of 250 mM ammonium sulfate, pH 6.5 were used. Twenty milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port and was collected in a glass bottle and was then concentrated by tangent flow filtration. The buffer was changed into a histidine/sucrose buffer (10 mM histidine, 9.2% sucrose, pH 6.5) by tangent flow filtration. The formulation was then sterilized by filtration through a 0.22 μm filter. The Z-average particle size was 32.9 nm for CPT307B. The volume-weighted particle size distribution of CPT307B determined by dynamic light scattering (Malvern Zetasizer Nano ZS) is shown in FIG. 2.

TABLE 2

Lipid Composition of Example 2.

| Component | CPT307B % (molar)* |
|---|---|
| DOPC | 73.6 |
| Cholesterol | 20 |
| mPEG2000-DSPE | 6.4 |
| DOCE | 6.0 |

*The value represents the molar % of each component vs. total lipids.

Example 3: Preparation of Combination Liposomal Formulation CPT307AB

Liposomal formulation CPT307AB was prepared by mixing CPT307A (see Example 1) and CPT307B (see Example 2) at a 1:1 molar ratio (or 1:1.5 w/w ratio) of DXR encapsulated in CPT307A and DOCE encapsulated in CPT307B. For instance, CPT307AB was prepared by mixing 12.07 mL of CPT307A containing 1.74 mg/mL of DXR and 12.26 mL of CPT307B containing 2.57 mg/mL of DOCE. The mixture was gently swirled to allow for complete mixing. The composition (% molar) of the CPT307AB lipid solution is illustrated in Table 3. The final concentrations of DXR and DOCE in CPT307AB were 0.86 mg/mL and 1.29 mg/mL, respectively.

TABLE 3

Lipid Composition of Example 3.

| Component | CPT307AB % (molar)* |
|---|---|
| DOPC | 73.6 |
| Cholesterol | 20 |
| mPEG2000-DSPE | 6.4 |
| DXR | 4.1 |
| DOCE | 4.1 |

*The value represents the molar % of each component vs. total lipids.

Example 4: Preparation of Liposomal Formulation CPT319A

CPT319A comprises of DOPC, cholesterol, 3β-[N—(N',N'-dimethylaminoethane)-carbamoyl]cholesterol hydrochloride (DC-Cholesterol), and mPEG2000-DSPE. DC-Cholesterol is a cationic derivative of cholesterol that brings positive surface charges to liposome and thus dramatically the in vivo distribution of the liposome. To make the liposome, a lipid solution was prepared firstly by dissolving 1800 mg of DOPC, 300 mg of cholesterol, 420 mg of DC-cholesterol and 600 mg of mPEG2000-DSPE in 60 mL of anhydrous ethanol. In addition, three aqueous solutions of 250 mM ammonium sulfate, pH 6.5 were used. Twenty milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port was collected in a glass bottle and was then concentrated by tangent flow filtration. The buffer was changed into a histidine/sucrose buffer (10 mM histidine, 9.2% sucrose, pH 6.5) by tangent flow filtration.

Figure 3:
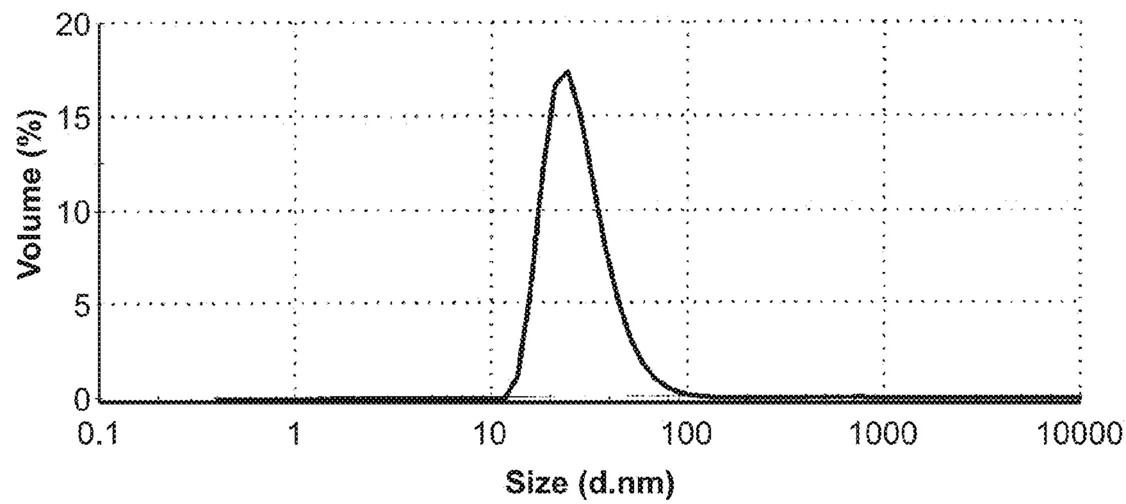
FIG. 3 illustrates volume-weighted particle size distribution of liposomal formulation CPT319A determined by dynamic light scattering.

Liposomal formulation CPT319A was prepared by loading DXR into the empty liposomes. Thirty milliliters of the empty liposomes containing lipids at 33.5 mg/mL was mixed with 83.6 mg of DXR that had been pre-dissolved in the histidine/sucrose buffer, and incubated at 42° C. for 3 hours, 94.6% of DXR was encapsulated. The encapsulated liposome was then sterilized by filtration through a 0.22 μm filter. The composition (% molar) of the CPT319A illustrated in Table 4. The final Z-average of the particle size of the loaded liposome was 43.6 nm. The volume-weighted particle size distribution of CPT319A determined by dynamic light scattering (Malvern Zetasizer Nano ZS) is shown in FIG. 3.

TABLE 4

Lipid Composition of Example 4.

| Component | CPT319A % (molar)* |
|---|---|
| DOPC | 61.7 |
| Cholesterol | 17.7 |
| DC-Cholesterol | 15.2 |
| mPEG2000-DSPE | 5.4 |
| DXR | 10.3 |

*The value represents the molar % of each component vs. total lipids.

Example 5: Preparation of Liposomal Formulation CPT319B

Figure 4:
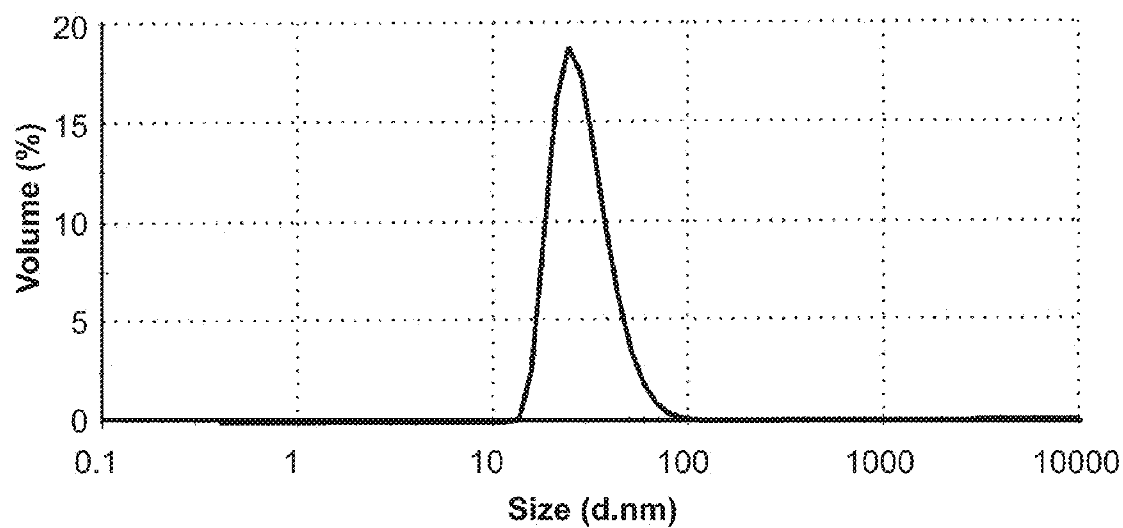
FIG. 4 illustrates volume-weighted particle size distribution of liposomal formulation CPT319B determined by dynamic light scattering.
Figure 5:
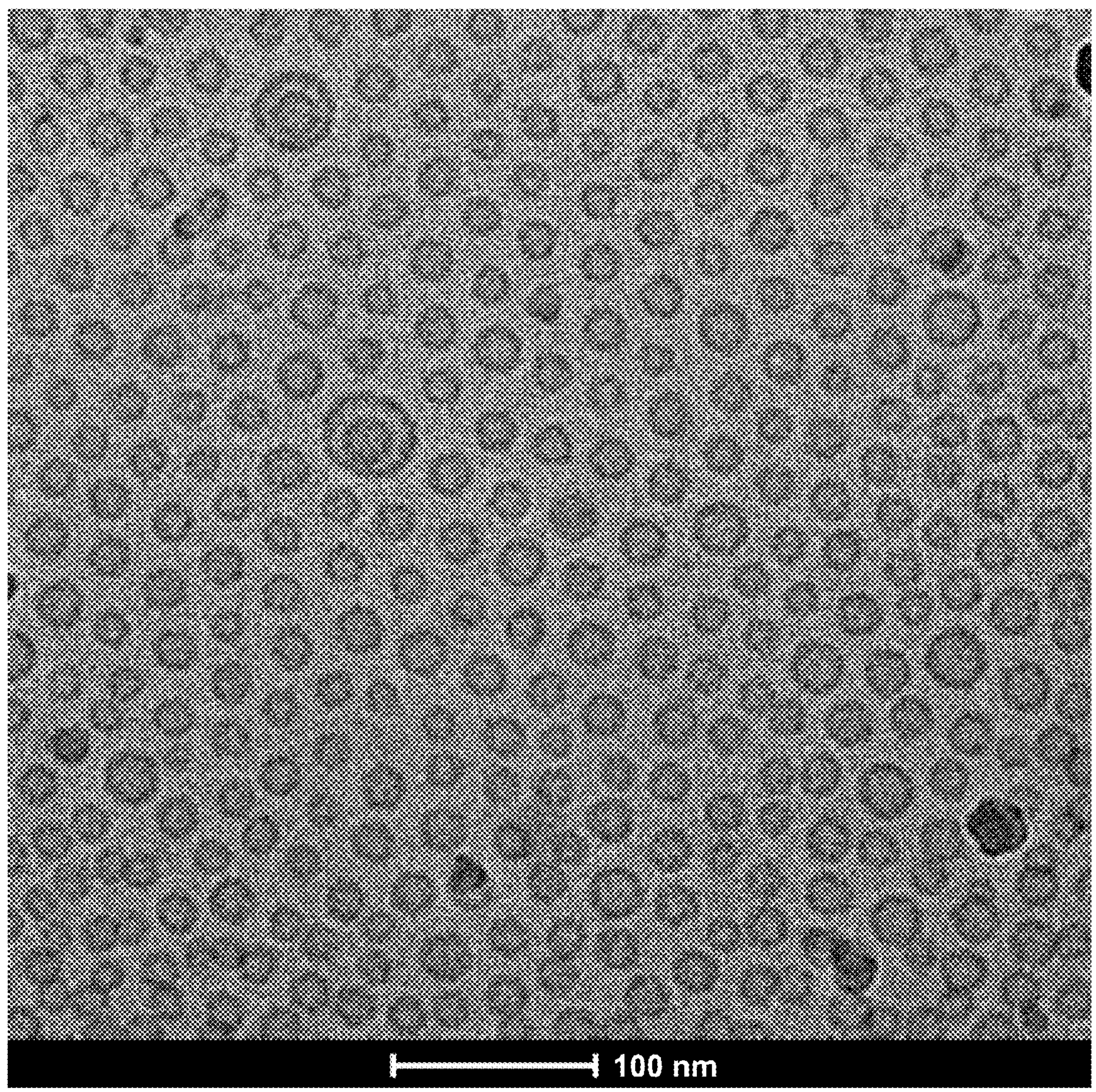
FIG. 5 presents a cryo transmission electron microscopy (TEM) image of liposomal formulation CPT319B.
Figure 6:
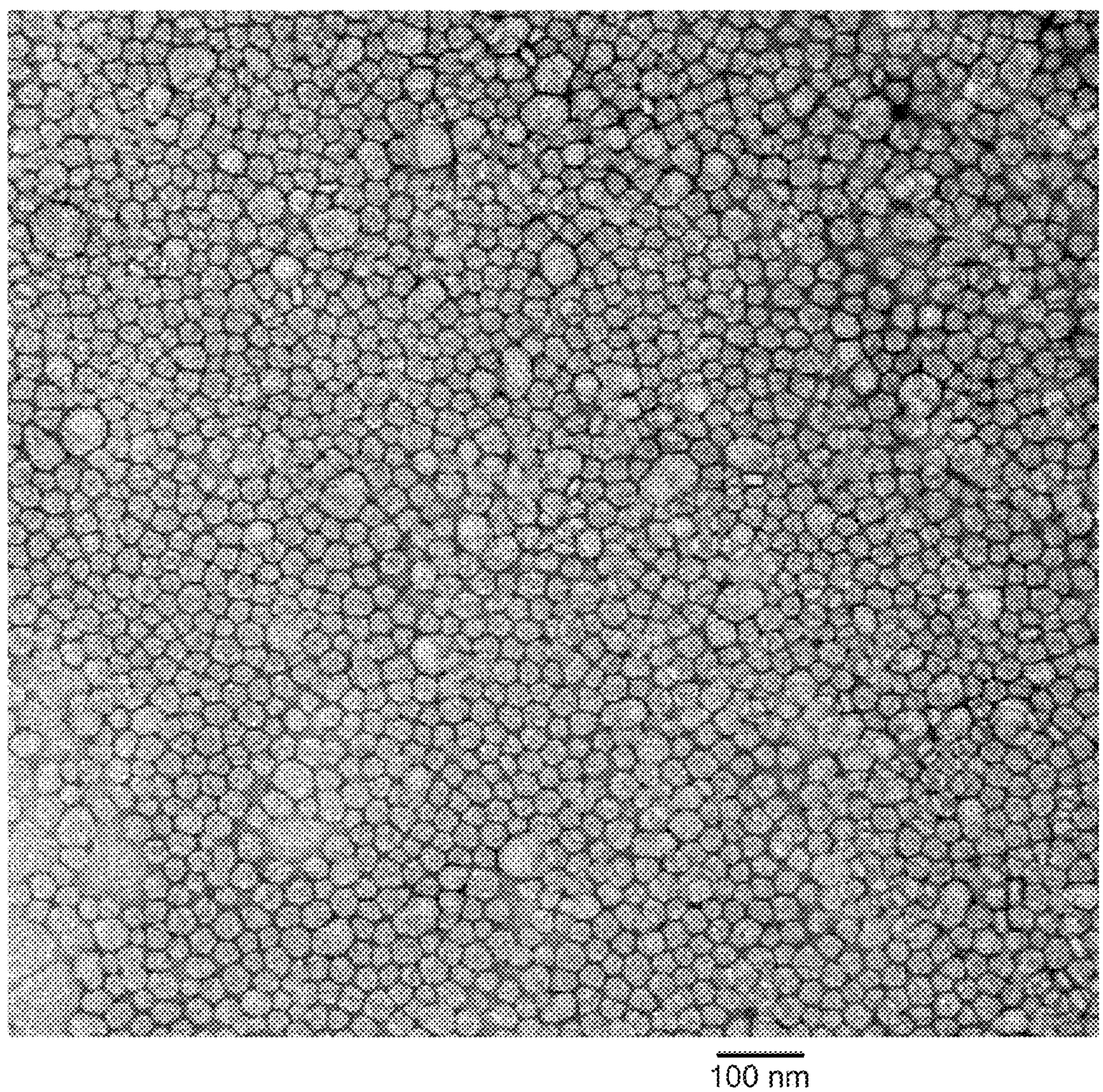
FIG. 6 presents a negative stained TEM image of liposomal formulation CPT319B.

CPT319B comprises of DOPC, cholesterol, 3β-[N—(N',N'-dimethylaminoethane)-carbamoyl]cholesterol hydrochloride (DC-Cholesterol), and mPEG2000-DSPE. DC-Cholesterol is a cationic derivative of cholesterol that brings positive surface charges to liposome and thus dramatically the in vivo distribution of the liposome. The lipids composition is identical to CPT319A. To make CPT319B, a lipid/DOCE solution was prepared by dissolving 1848 mg of DOPC, 303 mg of cholesterol, 423 mg of DC-Cholesterol, 605 mg of mPEG2000-DSPE, and 154 mg of DOCE in 61.5 mL of anhydrous ethanol. The composition (% molar) of the CPT319B lipid solution is illustrated in Table 5. In addition, three aqueous solutions of 250 mM ammonium sulfate, pH 6.5 were used. Twenty milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port was collected in a glass bottle and was then concentrated by tangent flow filtration. The buffer was changed into a histidine/sucrose buffer (10 mM histidine, 9.2% sucrose, pH 6.5) by tangent flow filtration. The formulation was then sterilized by filtration through a 0.22 μm filter. The volume-weighted particle size distribution of CPT319B determined by dynamic light scattering testing with a Malvern Zetasizer Nano ZS is shown in FIG. 4. The Cryo-TEM images of CPT319B are shown in FIG. 5. The particles exhibited overwhelmingly spherical unilamellar morphology with homogenous particle size. The negative stained TEM image of CPT319B is shown in FIG. 6, which further presents the small spherical and homogenous particles.

TABLE 5

Lipid Composition of Example 5.

| Component | CPT319B % (molar)* |
|---|---|
| DOPC | 61.7 |
| Cholesterol | 17.7 |
| DC-Cholesterol | 15.2 |
| mPEG2000-DSPE | 5.4 |
| DOCE | 3.5 |

*The value represents the molar % of each component vs. total lipids.

Example 6: Preparation of Combination Liposomal Formulation CPT319AB

Liposomal formulation CPT319AB was prepared by mixing CPT319A (see Example 4) and CPT319B (see Example 5) at a 1:1 molar ratio (or 1:1.5 w/w ratio) of DXR encapsulated in CPT319A and DOCE encapsulated in CPT319B. For instance, CPT319AB was prepared by mixing 13.7 mL of CPT319A containing 1.24 mg/mL of DXR and 11.7 mL of CPT319B containing 2.18 mg/mL of DOCE. The mixture was gently swirled to allow for complete mixing. The composition (% molar) of the CPT319AB lipid solution is illustrated in Table 6. The final concentrations of DXR and DOCE in CPT319AB were 0.67 mg/mL and 1.0 mg/mL, respectively.

TABLE 6

Lipid Composition of Example 6.

| Component | CPT319AB % (molar)* |
|---|---|
| DOPC | 61.7 |
| Cholesterol | 17.7 |
| DC-Cholesterol | 15.2 |
| mPEG2000-DSPE | 5.4 |
| DXR | 2.6 |
| DOCE | 2.6 |

*The value represents the molar % of each component vs. total lipids.

Example 7: Preparation of Liposomal Formulation CPT317A

CPT317A comprises of the same type of lipids as CPT319A while lipids ratio is changed (increased cholesterol and decreased DOPC and DC-cholesterol). To make CPT317A, a lipid solution was prepared by dissolving 600 mg of DOPC, 140 mg of cholesterol, 84 mg of DC-Cholesterol, and 200 mg of mPEG2000-DSPE in 20 mL of anhydrous ethanol. In addition, three aqueous solutions of 250 mM ammonium sulfate, pH 6.5 were used. Twenty milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port was collected in a glass bottle and was then concentrated by tangent flow filtration. The buffer was changed into a histidine/sucrose buffer (10 mM histidine, 9.2% sucrose, pH 6.5) by dialysis.

Liposomal formulation CPT317A was prepared by loading DXR into the empty liposomes. Fifteen milliliters of the empty liposomes containing lipids at 40.6 mg/mL was mixed with 50.7 mg of DXR and incubated at 42° C. for 3 hours, 99.2% of DXR was encapsulated. The encapsulated liposome was then sterilized by filtration through a 0.22 μm filter. The Z-average particle size of the loaded liposome determined by dynamic light scattering (Malvern Zetasizer Nano ZS) was 37.6 nm. The composition (% molar) of the CPT317A is illustrated in Table 7,

TABLE 7

Lipid Composition of Example 7.

| Component | CPT317A % (molar)* |
|---|---|
| DOPC | 56.6 |
| Cholesterol | 26.9 |
| DC-Cholesterol | 11.6 |
| mPEG2000-DSPE | 5.0 |
| DXR | 11.6 |

*The value represents the molar % of each component vs. total lipids.

Example 8: Preparation of Liposomal Formulation CPT317B

The liposome composition of CPT317B is identical to CPT317A. To make CPT317B, a lipid/DOCE solution was prepared by dissolving 600 mg of DOPC, 140 mg of cholesterol, 84 mg of DC-Cholesterol, 200 mg of mPEG2000-DSPE, and 50 mg of DOCE in 20 mL of anhydrous ethanol. The composition (% molar) of the CPT317B is illustrated in Table 8. In addition, three aqueous solutions of 250 mM ammonium sulfate, pH 6.5 were used. Twenty milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port was collected in a glass bottle and was then concentrated by tangent flow filtration. The buffer was changed into a histidine/sucrose buffer (10 mM histidine, 9.2% sucrose, pH 6.5) by tangent flow filtration. The formulation was then sterilized by filtration through a 0.22 μm filter. The Z-average particle size determined by dynamic light scattering (Malvern Zetasizer Nano ZS) was 47.9 nm.

TABLE 8

| Lipid Composition of Example 8. | |
|---|---|
| Component | CPT317B % (molar)* |
| DOPC | 56.6 |
| Cholesterol | 26.9 |
| DC-Cholesterol | 11.6 |
| mPEG2000-DSPE | 5.0 |
| DOCE | 4.6 |

*The value represents the molar % of each component vs. total lipids.

Example 9: Preparation of Combination Liposomal Formulation CPT317AB

Liposomal formulation CPT317AB was prepared by mixing CPT317A (see Example 7) and CPT317B (see Example 8) at a 1:1 molar ratio (or 1:1.5 w/w ratio) of DXR encapsulated in CPT317A and DOCE encapsulated in CPT317B. For instance, CPT317AB was prepared by mixing 2.48 mL of CPT317A containing 1.43 mg/mL of DXR and 2.86 mL of CPT317B containing 1.86 mg/mL of DOCE. The mixture was gently swirled to allow for complete mixing. The composition (% molar) of the CPT317AB lipid solution is illustrated in Table 9. The final concentrations of DXR and DOCE in CPT317AB were 0.66 mg/mL and 1.0 mg/mL, respectively.

TABLE 9

| Lipid Composition of Example 9. | |
|---|---|
| Component | CPT317AB % (molar) |
| DOPC | 56.6 |
| Cholesterol | 26.9 |
| DC-Cholesterol | 11.6 |
| mPEG2000-DSPE | 5.0 |
| DXR | 3.3 |
| DOCE | 3.3 |

*The value represents the molar % of each component vs. total lipids.

Example 10: Preparation of Liposomal Formulation CPT308B

Different from other exemplary formulations above those contain a monounsaturated lipid DOPC, CPT308B contains a polyunsaturated lipid-Soy PC. It was found that compared to DOPC, Soy PC further increases DOCE encapsulation capacity of liposome. To make CPT308B, two milliliters of the lipids/DOCE solution was prepared by first dissolving 30 mg of L-α-phosphatidylcholine (Soy PC), 10 mg of cholesterol, 10 mg of mPEG2000-DSPE, and 6 mg of DOCE in 2 mL of anhydrous ethanol. The composition (% molar) of the lipid formulation of CPT308B is illustrated in Table 10. In addition, three aqueous solutions of 250 mM ammonium sulfate, pH 6.5 were used. Two milliliters of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port was collected in a glass vial. The buffer was changed into a histidine/sucrose buffer (10 mM histidine, 9.2% sucrose, pH 6.5) by dialysis. The formulation was then sterilized by filtration through a 0.22 μm filter. The Z-average particle size of CPT308B determined by dynamic light scattering (Malvern Zetasizer Nano ZS) was 34.7 nm.

TABLE 10

| Lipid Composition of Example 10. | |
|---|---|
| Component | CPT308B % (molar)* |
| Soy PC | 57.0 |
| Cholesterol | 38.1 |
| mPEG2000-DSPE | 4.9 |
| DOCE | 10.9 |

*The value represents the molar % of each component vs. total lipids.

Example 11: Preparation of Liposomal Formulation CPT309B

In order to further improve DOCE encapsulation capacity of the liposome containing Soy PC, the molar ratio of Soy PC in CPT309B is increased while the molar ratio of cholesterol is decreased. To make CPT309B, two milliliters of the lipids/DOCE solution was prepared by dissolving 30 mg of Soy PC, 4 mg of cholesterol, 10 mg of mPEG2000-DSPE, and 6 mg of DOCE in 2 mL anhydrous ethanol. The composition (% molar) of the lipid formulation CPT309B lipid solution is illustrated in Table 11. In addition, three aqueous solutions of 250 mM ammonium sulfate, pH 6.5 were used. Two milliliters of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port was collected in a glass vial. The buffer was changed into a histidine/sucrose buffer (10 mM histidine, 9.2% sucrose, pH 6.5) by dialysis. The formulation was then sterilized by filtration through a 0.22 μm filter. The Z-average particle size of CPT309B determined by dynamic light scattering (Malvern Zetasizer Nano ZS) was 35.0 nm.

TABLE 11

| Lipid Composition of Example 11. | |
|---|---|
| Component | CPT309B % (molar) |
| Soy PC | 73.9 |
| Cholesterol | 19.7 |
| mPEG2000-DSPE | 6.4 |
| DOCE | 14.2 |

*The value represents the molar % of each component vs. total lipids.

Example 12: Preparation of Liposomal Formulation CPT313B

In CPT313B, cholesterol is completely substituted by DC-cholesterol. To make CPT313B, a lipid/DOCE solution was prepared by dissolving 33 mg of Soy PC, 20.5 mg of DC-Cholesterol, 11 mg of mPEG2000-DSPE, and 4.4 mg of DOCE in 2.2 mL of anhydrous ethanol. The composition (% molar) of the CPT313B is illustrated in Table 12. In addition, three aqueous solutions of 250 mM ammonium sulfate, pH 6.5 were used. Two milliliters of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port was collected in a glass vial. The buffer was changed into a histidine/sucrose buffer (10 mM histidine, 9.2% sucrose, pH 6.5) by dialysis. The formulation was then sterilized by filtration through a 0.22 μm filter. The Z-average particle size of CPT313B determined by dynamic light scattering (Malvern Zetasizer Nano ZS) was 37.4 nm.

TABLE 12

Lipid Composition of Example 12.

| Component | CPT313B % (molar)* |
|---|---|
| Soy PC | 50.4 |
| mPEG2000-DSPE | 4.4 |
| DC-cholesterol | 45.2 |
| DOCE | 6.5 |

*The value represents the molar % of each component vs. total lipids.

Example 13: Preparation of Liposomal Formulation CPT323B

CPT323C comprises of DOPC, cholesterol, DC-cholesterol but in the absence of pegylated lipid, indicating that pegylated lipid is optional to the formulation. To make CPT323B, a lipid/DOCE solution was prepared by dissolving 300 mg of DOPC, 50 mg of cholesterol, 70 mg of DC-Cholesterol, and 25 mg of DOCE in 10 mL of anhydrous ethanol. The composition (% molar) of the CPT323B is illustrated in Table 13. In addition, three aqueous solutions of 250 mM ammonium sulfate, pH 6.5 were used. Ten milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port was collected in a glass bottle and was then concentrated by tangent flow filtration. The buffer was changed into a histidine/sucrose buffer (10 mM histidine, 9.2% sucrose, pH 6.5) by dialysis. The formulation was then sterilized by filtration through a 0.22 μm filter. The Z-average particle size determined by dynamic light scattering (Malvern Zetasizer Nano ZS) of CPT323B was 47.5 nm.

TABLE 13

Lipid Composition of Example 13.

| Component | CPT323B % (molar)* |
|---|---|
| DOPC | 59.5 |
| Cholesterol | 20.1 |
| DC-Cholesterol | 20.3 |
| DOCE | 4.8 |

*The value represents the molar % of each component vs. total lipids.

Example 14: Preparation of Liposomal Formulation CPT324B

Different from other exemplary formulations, CPT324B contains a polyunsaturated lipid-Soy PC for a higher DOCE capacity, and a cationic lipid DOTAP other than DC-cholesterol. To make CPT324B, a lipid/DOCE solution was prepared by dissolving 60 mg of Soy PC, 40 mg of cholesterol, 60 mg of 1,2-dioleoyl-3-trimethylammonium-propane (chloride salt) (DOTAP), 40 mg of mPEG2000-DSPE, and 25 mg of DOCE in 10 mL of anhydrous ethanol. The composition (% molar) of the CPT324B is illustrated in Table 14. In addition, three aqueous solutions of 250 mM ammonium sulfate, pH 6.5 were used. Ten milliliter of each of the above four solutions was loaded into a 20 mL syringe. Each syringe was connected to an inlet port of a five-port manifold by tubing. Through the tubing, the solutions in the syringes were pumped into the mixing chamber of the manifold by a syringe pump. The liposome solution exited through an outlet port was collected in a glass bottle and was then concentrated by tangent flow filtration. The buffer was changed into a histidine/sucrose buffer (10 mM histidine, 9.2% sucrose, pH 6.5) by dialysis. The formulation was then sterilized by filtration through a 0.22 μm filter. The Z-average particle size of CPT324B determined by dynamic light scattering (Malvern Zetasizer Nano ZS) was 39.0 nm.

TABLE 14

Lipid Composition of Example 14.

| Component | CPT324B % (molar)* |
|---|---|
| Soy PC | 27.6 |
| Cholesterol | 36.9 |
| mPEG2000-DSPE | 4.8 |
| DOTAP | 30.7 |
| DOCE | 11.0 |

*The value represents the molar % of each component vs. total lipids.

Example 15: Combination Liposome CPT319AB Augments Efficacy Against Non-Small Cell Lung Cancer (NSCLC)

Figure 7:
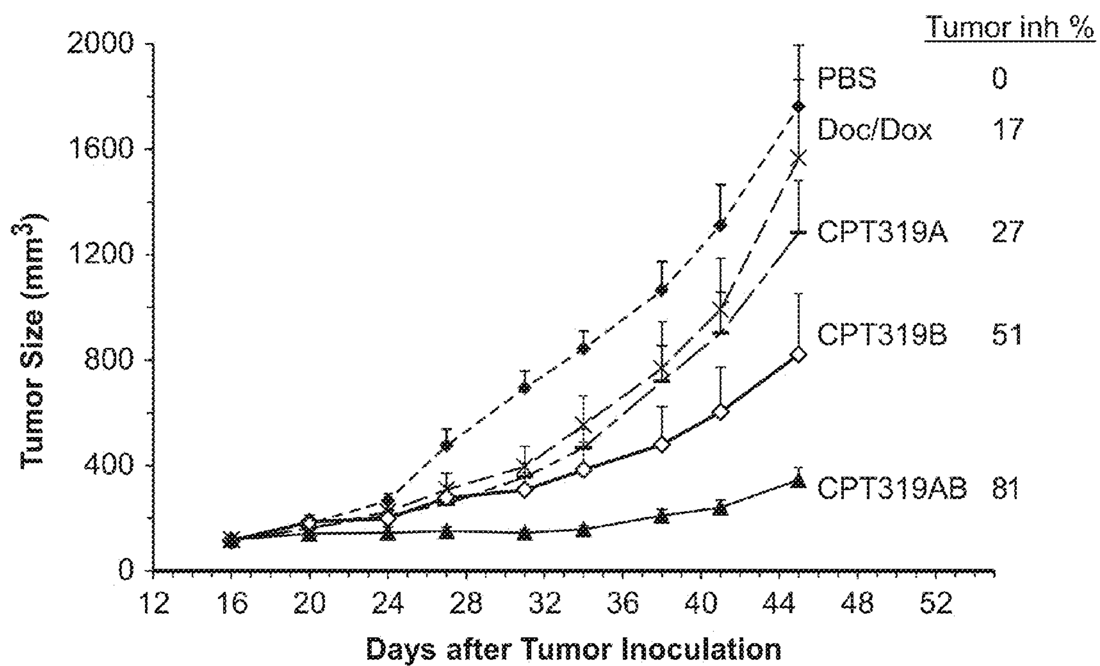
FIG. 7 illustrates non-small cell lung cancer (NSCLC) tumor growth curves and tumor weight inhibition percentages (TW Inh %) after administration with liposomal formulations (CPT319A, CPT319B, or CPT319AB) or non-liposomal formulations of docetaxel/doxorubicin, compared to the control group.

Female Balb/c nude mice ranging from 6-8 weeks of age were inoculated subcutaneously on the right flank with NSCLC cell line A549 tumor cells ($1\times10^7$ cells/mouse) in 0.1 mL phosphate buffered saline (PBS) for tumor development. On Day 16 following tumor cell inoculation (tumor size was approximately 117 $mm^3$), treatments were started with formulations of CPT319A at 5 mg/kg doxorubicin, CPT319B at 7.5 mg/kg docetaxel, CPT319AB at 5 mg/kg doxorubicin/7.5 mg/kg docetaxel, or the non-liposomal combination formulation of 5 mg/kg doxorubicin/7.5 mg/kg docetaxel by intravenous (IV) injection through the tail vein. Three additional treatments were administered on Day 20, Day 27, and Day 34. The study was terminated on Day 45. The tumor growth curves and tumor weight inhibition percentages (TW Inh %) on Day 45 of the formulations compared to the PBS control group are shown in FIG. 7. All of the liposomal formulations were more efficacious than the non-liposomal combination of DOCE/DXR. In addition, the combination liposome, CPT319AB was the most efficacious in this example. Compared to the PBS control group, the combination liposomal formulation CPT319AB reduced 81% of the tumor weight that was significantly more efficacious than the 51% of DOCE liposome CPT319B, 27% of DXR liposome CPT319A, and 17% of the non-liposomal combination of DOCE/DXR.

Example 16: Combination Liposome CPT307AB Augments Efficacy Against NSCLC

Figure 8:
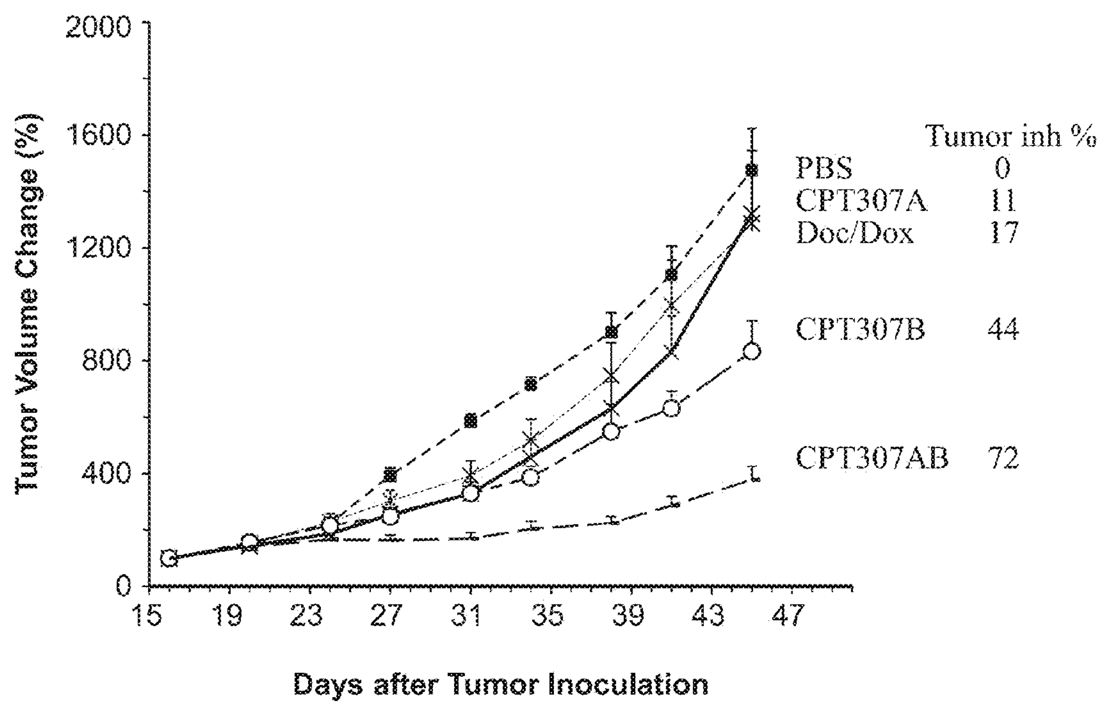
FIG. 8 illustrates NSCLC tumor growth curves and tumor weight inhibition percentages (TW Inh %) after administration with liposomal formulations (CPT307A, CPT307B, or CPT307AB) or non-liposomal formulations of docetaxel/doxorubicin, compared to the control group.

Female Balb/c nude mice ranging from 6-8 weeks of age were inoculated subcutaneously on the right flank with NSCLC cell line A549 tumor cells ($1\times10^7$ cells/mouse) in 0.1 mL phosphate buffered saline (PBS) buffer for tumor development. On Day 16 following tumor cell inoculation (tumor size was approximately 117 $mm^3$), treatments were started with formulations of CPT307A at 5 mg/kg doxorubicin, CPT307B at 7.5 mg/kg docetaxel, CPT307AB at 5 mg/kg doxorubicin/7.5 mg/kg docetaxel, or the non-liposomal combination formulation of 5 mg/kg doxorubicin/7.5 mg/kg docetaxel by intravenous (IV) injection through the tail vein. Three additional treatments were administered on Day 20, Day 27, and Day 34. The study was terminated on Day 45. The tumor growth curves and tumor weight inhibition percentages (TW Inh %) on Day 45 of the formulations compared to the PBS control group are shown in FIG. 8. All of the liposomal formulations were more efficacious than the non-liposomal combination of DOCE/DXR. In addition, the combination liposome, CPT307AB was the most efficacious in this example. Compared to the PBS control group, the combination liposomal formulation CPT307AB reduced 72% of the tumor weight that was significant more efficacious than the 44% of DOCE liposome CPT307B, 11% of DXR liposome CPT307A, and 17% of the non-liposomal combination of DOCE/DXR.

Figure 9:
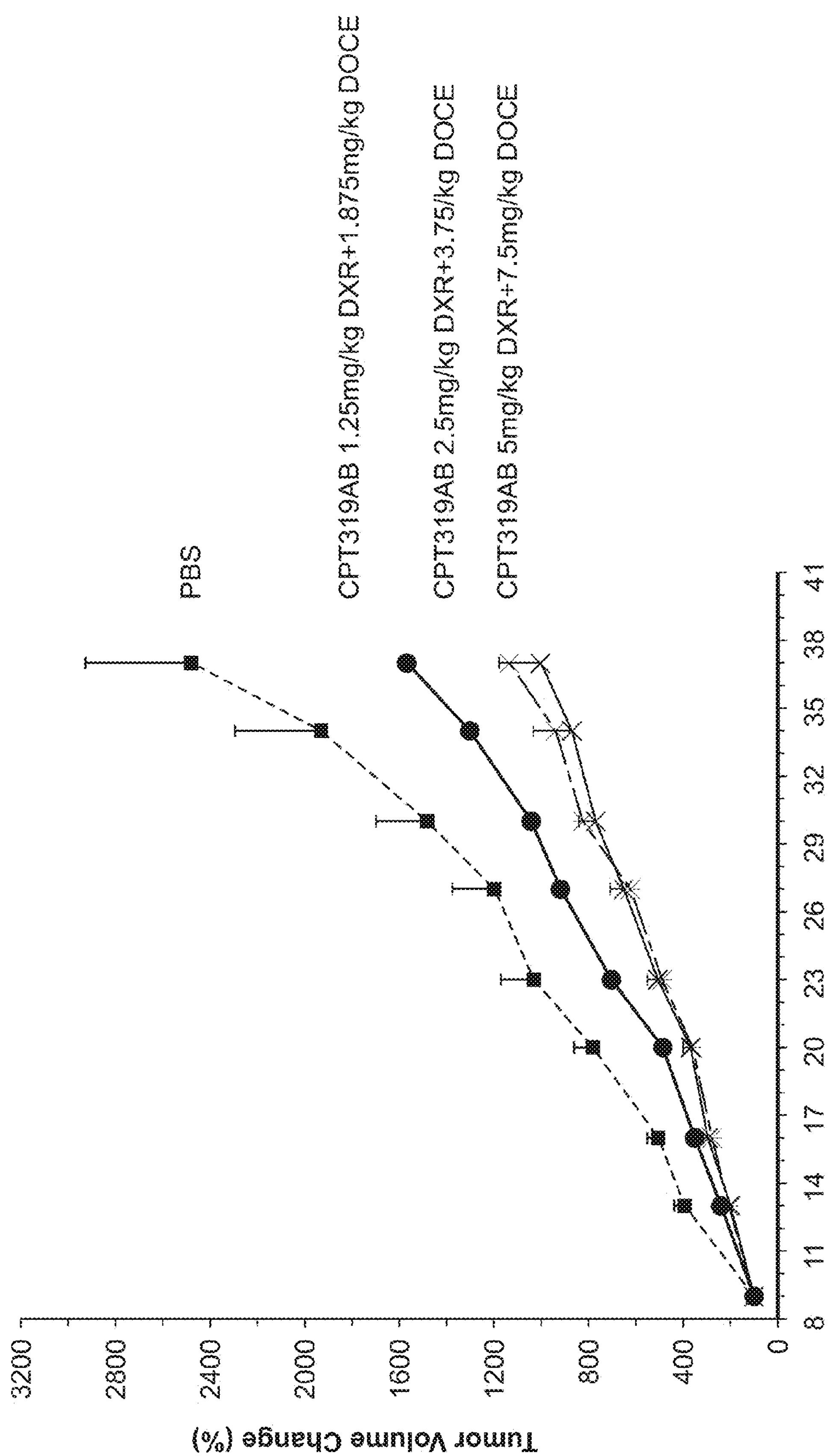
FIG. 9 illustrates colon cancer tumor growth curves after administration with three different doses of liposomal formulation (CPT319AB), compared to the control group.

Example 17: Antitumor Activity of Combination Liposome CPT319AB Against Human Colon Cancer in Xenograft Mouse Model Female Balb/c nude mice ranging from 6-8 weeks of age were inoculated subcutaneously at the right flank with human colon cancer cell line HCT-116 tumor cells ($5\times10^6$ cells/mouse) in 0.1 mL PBS buffer for tumor development. On Day 9 following tumor cell inoculation (tumor size was approximately 141 $mm^3$), treatments were started with formulations of CPT319AB at 3 different doses: 5 mg/kg doxorubicin/7.5 mg/kg docetaxel, 2.5 mg/kg doxorubicin/3.75 mg/kg docetaxel, or 1.25 mg/kg doxorubicin/1.875 mg/kg docetaxel by intravenous (IV) injection through the tail vein. Two additional treatments were administered on Day 16 and Day 23. The study was terminated on Day 37. The tumor growth curves shown in FIG. 9 illustrate dose responses of the HCT-116 tumor cells to the liposomal formulations (which are compared to the vehicle control). Compared to the vehicle control, tumor weight was inhibited by 59, 52, and 29% in the treatment groups (doses from high to low).

Figure 10:
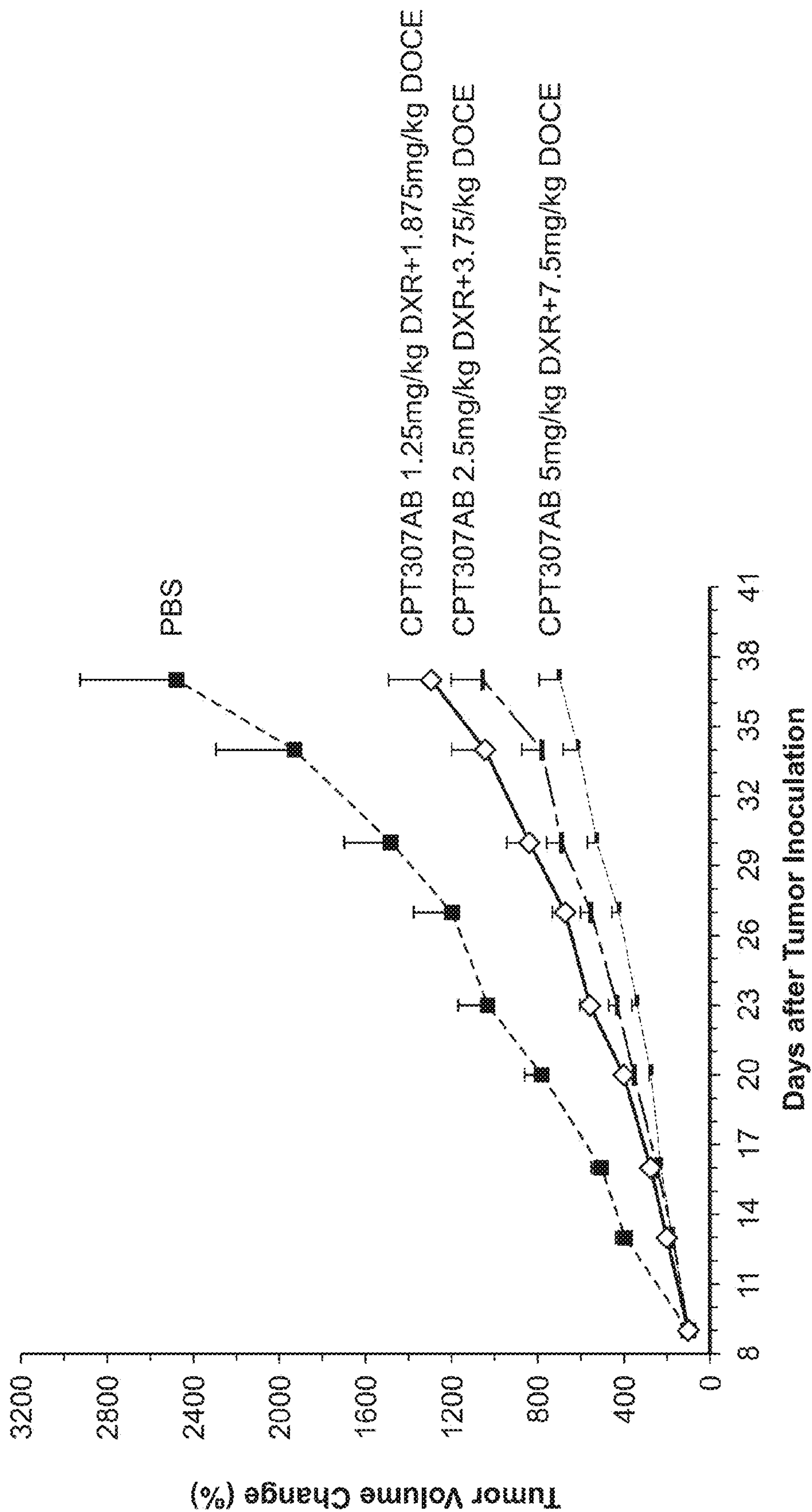
FIG. 10 illustrates colon cancer tumor growth curves after administration with three different doses of liposomal formulation (CPT307AB), compared to the control group.

Example 18: Antitumor Activity of Combination Liposome CPT307AB Against Human Colon Cancer in Xenograft Mouse Model Female Balb/c nude mice ranging from 6-8 weeks of age were inoculated subcutaneously at the right flank with human colon cancer cell line HCT-116 tumor cells ($5\times10^6$ cells/mouse) in 0.1 mL PBS buffer for tumor development. On Day 9 following tumor cell inoculation (tumor size was approximately 141 $mm^3$), treatments were started with formulations of CPT307AB at 3 different doses: 5 mg/kg doxorubicin/7.5 mg/kg docetaxel, 2.5 mg/kg doxorubicin/3.75 mg/kg docetaxel, or 1.25 mg/kg doxorubicin/1.875 mg/kg docetaxel by intravenous (IV) injection through the tail vein. Two additional treatments were administered on Day 16 and Day 23. The study was terminated on Day 37. The tumor growth curves shown in FIG. 10 illustrate dose responses of the HCT-116 tumor cells to the liposomal formulations (which are compared to the vehicle control). Compared to the vehicle control, tumor weight was inhibited by 64, 52, and 45% in the treatment groups (doses from high to low).

Figure 11:
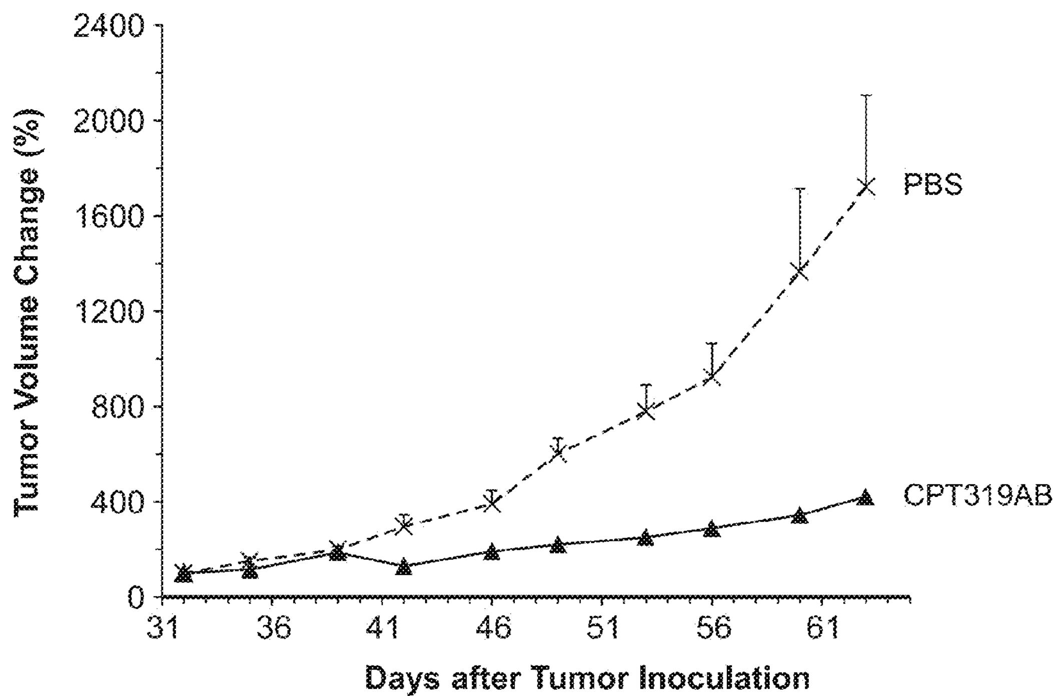
FIG. 11 illustrates hepatocellular carcinoma tumor growth curves after administration with liposomal formulation (CPT319AB), compared to the control group.

Example 19: Antitumor Activity of Combination Liposome CPT319AB Against Human Primary Hepatocellular Carcinoma in Xenograft Mouse Model Female SCID Beige mice ranging from 6-8 weeks of age were inoculated subcutaneously at the right flank with fragments of human primary hepatocellular carcinoma tumor (P3 WP HCC) for tumor development. On Day 32 after tumor inoculation (tumor size was approximately 143 $mm^3$), treatments were started with a formulation of CPT319AB at 5 mg/kg doxorubicin/7.5 mg/kg docetaxel by intravenous (IV) injection through the tail vein. Two additional treatments were made on Day 39 and Day 46. The study was terminated on Day 63. The tumor growth curves are shown in FIG. 11. CPT319AB reduced tumor weight by 68% compared to the vehicle control.

Figure 12:
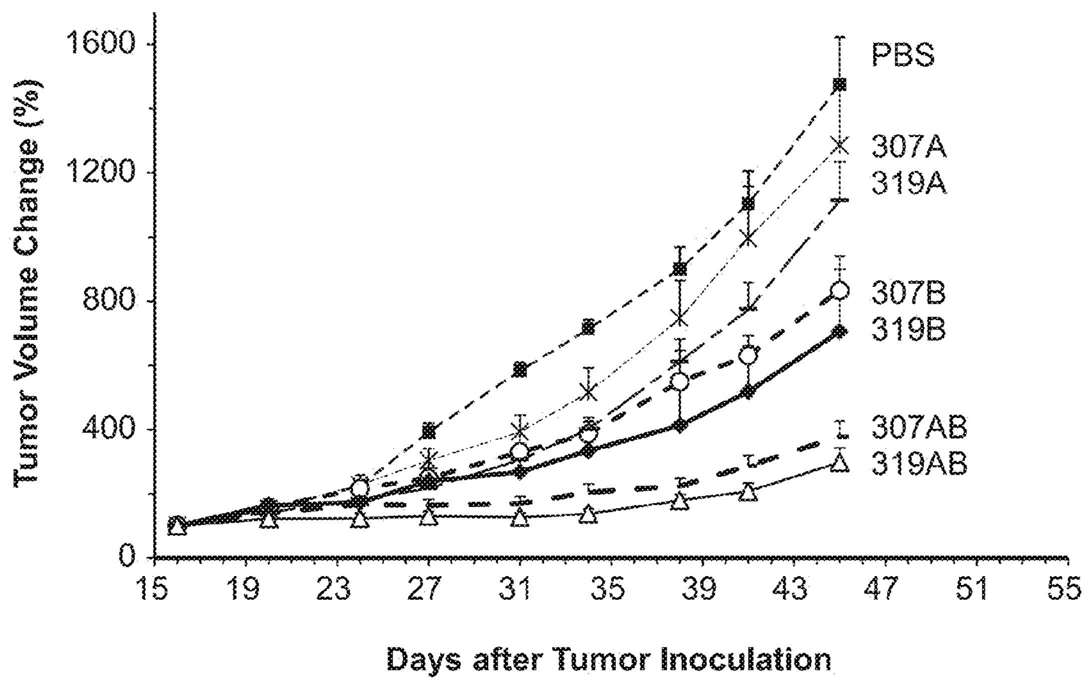
FIG. 12 illustrates NSCLC tumor growth curves after administration with liposomal formulations (CPT307A, B, or AB and CPT319A, B, or AB), compared to the control group.

Example 20: Cationic Lipid DC-Cholesterol Enhances the Antitumor Activity of Liposomes Against NSCLC Female Balb/c nude mice ranging from 6-8 weeks of age were inoculated subcutaneously at the right flank with NSCLC cell line A549 tumor cells ($1\times10^7$ cells/mouse) in 0.1 mL PBS buffer for tumor development. On Day 16 following tumor cell inoculation (tumor size was approximately 117 $mm^3$), treatments were started with formulations of CPT307A or CPT319A at 5 mg/kg doxorubicin, CPT307B or CPT319B at 7.5 mg/kg docetaxel, CPT307AB or CPT319AB at 5 mg/kg doxorubicin/7.5 mg/kg docetaxel, or the non-liposomal combination formulation of 5 mg/kg doxorubicin/7.5 mg/kg docetaxel by intravenous (IV) injection through the tail vein. Three additional treatments were made on Day 20, Day 27, and Day 34. The study was terminated on Day 45. The lipid compositions of the CPT307 (without DC-Cholesterol) and CPT319 (with DC-Cholesterol) formulations are shown in Table 15. The tumor growth curves are shown in FIG. 12. The tumor weight inhibition % on Day 45 is shown in Table 16.

The tumor inhibition rank order (from high to low) was: CPT319AB>CPT307AB>CPT319B>CPT307B>CPT319A>CPT307A>PBS. For each instance, CPT319 (with DC-Cholesterol) was more efficacious than CPT307 (without DC-Cholesterol). This indicates that the cationic lipid DC-cholesterol in CPT319 enhances the antitumor activity of the liposome formulations.

TABLE 15

Lipid Compositions of Example 20.

| Formulation | DC-cholesterol (molar %) | Cholesterol (molar %) | mPEG-DSPE (molar %) | DOPC (molar %) |
|---|---|---|---|---|
| CPT319 | 15 | 18 | 5 | 62 |
| CPT307 | 0 | 24 | 6 | 70 |

TABLE 16

Tumor Weight Inhibition % on Day 45 of Example 20

| Formulation | A | B | AB |
|---|---|---|---|
| CPT319 | 27% | 51% | 81% |
| CPT307 | 11% | 44% | 72% |

Figure 13:
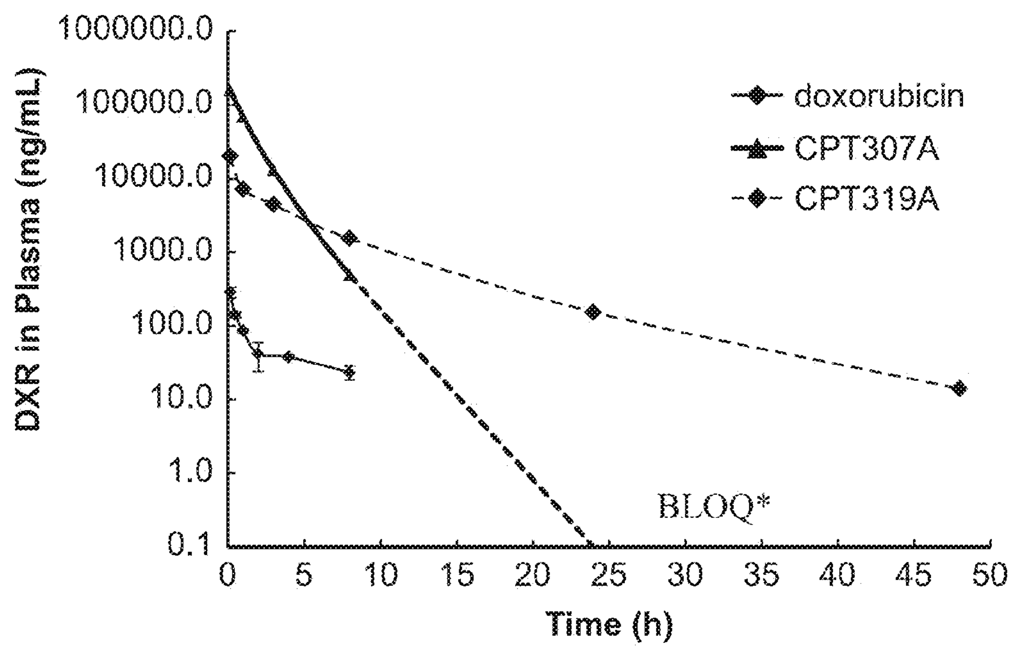
FIG. 13 illustrates plasma concentration curves of doxorubicin after administration with liposomal formulations (CPT307A or CPT319A), compared to non-liposomal formulations of docetaxel/doxorubicin. *BLOQ: Below Limit of Quantitation.

Example 21: Cationic Lipid DC-Cholesterol Increases the Half-Life ($t_{1/2}$) of DXR Male CD-1 mice ranging from 20-25 g body weight were split up into groups of three. Each mouse was administered with a single dose of CPT319A or CPT307A at 5 mg/kg DXR by intravenous (IV) injection through the tail vein. A non-liposomal combination of DXR was used as the control. Blood samples were collected at 0.167, 1, 3, 8, 24, and 48 h after the injection. DXR plasma concentration was determined by liquid chromatography-tandem mass spectrometry (LC-MS-MS). The plasma concentration curves of DXR are shown in FIG. 13 and the $t_{1/2}$ and area under the plasma concentration time curve (AUC) are provided in Table 17. *BLOQ: Below Limit of Quantitation. The non-liposomal DXR was cleared quickly from the blood and resulted in a very low AUC (688 h×ng/mL), whereas CPT319A and CPT307A increased AUC by 84 and 354 fold, respectively. Moreover, CPT319A exhibited a 5.5 h $t_{1/2}$ compared to the 1 h $t_{1/2}$ of CPT307A, indicating that the cationic lipid DC-Cholesterol in CPT319A improves PK of the formulation by increasing circulation time in the blood. The faster decrease of blood concentration for CPT319A compared to CPT307A in the first 3 h after injection indicates that the cationic charge of CPT319A causes a quicker distribution to other organs, such as the liver.

TABLE 17

$t_{1/2}$ and AUC values for Example 21.

| Formulation | $t_{1/2}$ (h) | AUC (h × ng/mL) |
|---|---|---|
| CPT319A | 5.5 | 57453 |
| CPT307A | 1.0 | 243243 |
| Naked DXR | | 688 |

Example 22: Programmable Liver Delivery of Liposome by Varying the Cationic Lipid DC-Cholesterol Composition in the Liposome In order to investigate the effects of cationic lipid DC-Cholesterol on in vivo distribution of liposomal DXR, the following three liposome formulations were used for the PK studies: 1) Doxil® (FDA approved liposomal DXR) containing no DC-Cholesterol, 2) CPT319A containing 15.3% DC-Cholesterol, and 3) CPT221 containing 38.3% DC-Cholesterol. The lipid compositions of the three formulations are shown in Table 18.

Figure 14:
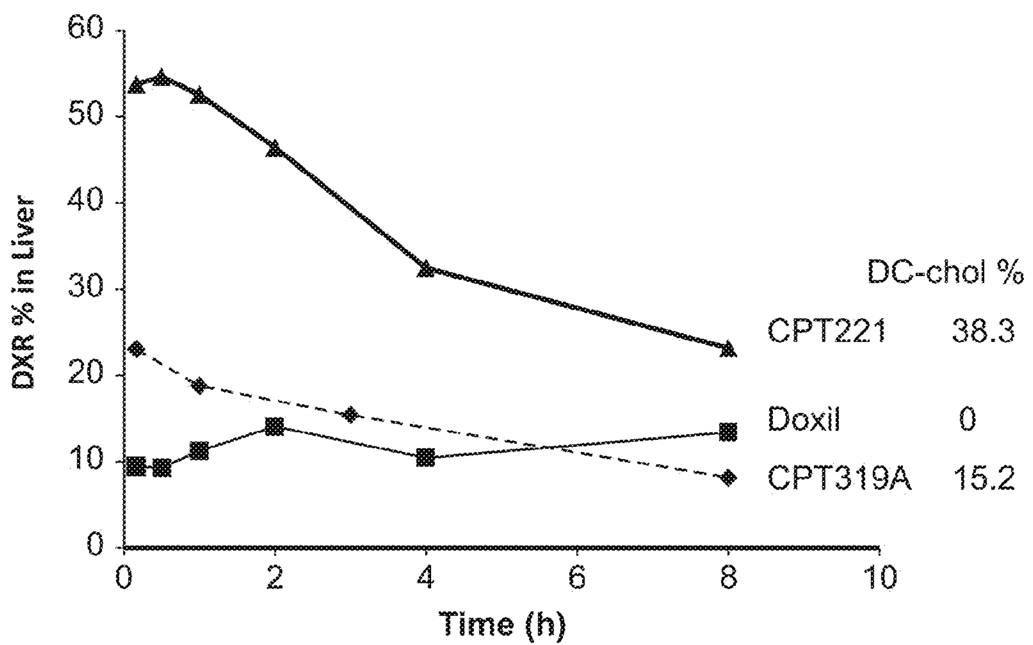
FIG. 14 illustrates liver concentration curves of doxorubicin after administration with liposomal formulations (Doxil®, CPT319A, or CPT221), as well as the DC-Cholesterol percentages of each liposomal formulations (DC-chol %).

Male CD-1 mice ranging from 20-25 g body weight were split up into groups of three. Each mouse was administered with a single dose of Doxil®, or CPT319A, or CPT221 at 5 mg/kg DXR by intravenous (IV) injection through the tail vein. The mice were sacrificed at designated times and their livers were collected. For the groups treated with Doxil® and CPT221, livers were collected at 0.167, 0.5, 1, 2, 4, and 8 h after the injection. For the group treated with CPT319A, livers were collected at 0.167, 1, 3, and 8 h after the injection. The quantity of DXR in the liver was determined using LC-MS-MS and the percentage of DXR in the liver was calculated against the total quantity of DXR administered. The liver concentration curves of DXR are shown in FIG. 14.

The cholesterol in Doxil® is completely substituted by DC-Cholesterol in CPT221, which resulted in a dramatic and rapid accumulation of DXR in the liver. For example, 10 min after the injection, about 54% of DXR of CPT221 was accumulated in the liver. The partial substitution of cholesterol by DC-Cholesterol in CPT319A corresponded to a 21% accumulation of DXR in the liver, while only 9.4% DXR of Doxil® accumulated in the liver. Therefore, programmable liver-targeting delivery can be achieved by controlling the molar ratio of a cationic lipid in the liposome.

TABLE 18

Lipid Compositions of Example 22.

| Component | Doxil ® | CPT319A | CPT221 |
|---|---|---|---|
| DOPC | | 61.7 | |
| DSPC | 56.7 | | 56.7 |
| Cholesterol | 38.3 | 17.7 | |
| DC-Cholesterol | | 15.2 | 38.3 |
| mPEG2000-DSPE | 5.0 | 5.4 | 5.0 |
| DXR | 17.1* | 10.3* | 13.7* |

*this value represents the molar % of DXR vs. total lipids.

The invention claimed is:

1. A pharmaceutical composition comprising two types of liposomes:

(i) a first liposome type comprising a first lipid layer comprising an unsaturated phospholipid, a cholesterol, and a first active pharmaceutical ingredient (API) comprising docetaxel in the first lipid layer; and (ii) a second liposome type comprising a second lipid layer, an aqueous interior, and a second API comprising doxorubicin crystallized in the aqueous interior, wherein the first liposome type does not comprise doxorubicin and the second liposome type does not comprise docetaxel and wherein the first lipid layer, the second lipid layer, or both the first and second lipid layers comprise:

about 20-75% (molar) unsaturated phospholipid;

about 10-60% (molar) cholesterol; and about 1-10% (molar) pegylated phospholipid.

2. The pharmaceutical composition of claim 1, wherein the first lipid layer, the second lipid layer, or both the first and second lipid layers consist essentially of the unsaturated phospholipid, a cholesterol, and a pegylated phospholipid.

3. The pharmaceutical composition of claim 1, wherein docetaxel is the only API in the first liposome type and/or doxorubicin is the only API in the second liposome type.

4. The pharmaceutical composition of claim 1, wherein:

the molar ratio of the first lipid layer components:docetaxel is about 100:1 to about 5:1; and the molar ratio of the second lipid layer components:doxorubicin is about 100:1 to about 5:1.

5. The pharmaceutical composition of claim 1, wherein the molar ratio of doxorubicin:docetaxel is about 10:1 to 1:10.

6. The pharmaceutical composition of claim 1, wherein the unsaturated phospholipid comprises a polyunsaturated phospholipid or a monounsaturated phospholipid.

7. The pharmaceutical composition of claim 1, wherein the cholesterol comprises a cationic cholesterol derivative.

8. The pharmaceutical composition of claim 1, wherein the first liposome further comprises a pegylated phospholipid.

9. The pharmaceutical composition of claim 1, formulated for intravenous administration.

10. The pharmaceutical composition of claim 1, wherein the Z-average particle size of the liposomes is about 20-120 nm.

11. The pharmaceutical composition of claim 1, wherein, upon intravenous administration to a subject, at least about 10% of the composition is delivered to the liver.

12. A method of treating a subject comprising administering an effective amount of the pharmaceutical composition of claim 1 to the subject, wherein the subject has a cancer.

13. The method of claim 12, wherein the cancer is a lung cancer; colon cancer; breast cancer; stomach cancer; esophagus cancer; prostate cancer; leukemia; head and neck cancer; pancreatic cancer; multiple myeloma; or liver cancer.

14. A method of making the pharmaceutical composition of claim 1, comprising:

(i) making a first liposome type by concurrently introducing a first lipid solution of an unsaturated phospholipid, a sterol, and docetaxel in ethanol through a first or plural inlet ports into a mixing chamber of a manifold and introducing a first aqueous solution through a second or plural inlet ports into the mixing chamber of the manifold, and the liposomes exit the mixing chamber through one or plural outlet chambers of the manifold, wherein the resulting first liposome type does not comprise doxorubicin;

(ii) making a second liposome type by concurrently introducing a second lipid solution in ethanol through a first or plural inlet ports into a mixing chamber of a manifold and introducing a first aqueous solution through a second or plural inlet ports into the mixing chamber of the manifold, and the liposomes exit the mixing chamber through one or plural outlet chambers of the manifold; and incubating the resulting liposomes with doxorubicin, wherein the resulting second liposome type does not comprise docetaxel; and (iii) combining predetermined amounts of the first liposome type and the second liposome type, thereby making the pharmaceutical composition of claim 1.

15. The pharmaceutical composition of claim 6, wherein the unsaturated phospholipid comprises soy phosphatidylcholine or 1,2-dioleoyl-sn-glycero-3-phosphatidylcholine (DOPC).

16. The pharmaceutical composition of claim 7, wherein the cholesterol comprises a dimethylaminoethanecarbamoyl-cholesterol (DC-cholesterol).

17. The method of claim 14, wherein the first lipid solution further comprises a pegylated phospholipid.

18. The pharmaceutical composition of claim 1, wherein both the first and second lipid layers comprise:

about 20-75% (molar) unsaturated phospholipid;

about 10-60% (molar) cholesterol; and about 1-10% (molar) pegylated phospholipid.

19. The pharmaceutical composition of claim 1, wherein both the first and second lipid layers comprise about 10-60% (molar) cationic lipid.

20. A pharmaceutical composition comprising two types of liposomes:

(i) a first liposome type comprising a first lipid layer comprising an unsaturated phospholipid, a cholesterol, and a first active pharmaceutical ingredient (API) comprising docetaxel in the first lipid layer; and (ii) a second liposome type comprising a second lipid layer, an aqueous interior, and a second API comprising doxorubicin crystallized in the aqueous interior, wherein the first liposome type does not comprise doxorubicin and the second liposome type does not comprise docetaxel and wherein both the first and second lipid layers comprise:

about 20-75% (molar) unsaturated phospholipid;

about 10-60% (molar) cholesterol; and about 1-10% (molar) pegylated phospholipid, and wherein the Z-average particle size of the liposomes is about 20-120 nm.

* * * * *